(12) United States Patent
Gross

(10) Patent No.: US 7,741,344 B2
(45) Date of Patent: Jun. 22, 2010

(54) PROCESS FOR PREPARING PURIFIED S-BEL AND R-BEL AND COMPOSITIONS THEREOF

(75) Inventor: Richard W. Gross, Chesterfield, MO (US)

(73) Assignee: Washington University in St. Louis, St. Louis, MO (US)

( * ) Notice: Subject to any disclaimer, the term of this patent is extended or adjusted under 35 U.S.C. 154(b) by 1120 days.

(21) Appl. No.: 10/508,064

(22) PCT Filed: Mar. 19, 2003

(86) PCT No.: PCT/US03/08834

§ 371 (c)(1),
(2), (4) Date: Apr. 6, 2005

(87) PCT Pub. No.: WO03/079996

PCT Pub. Date: Oct. 2, 2003

(65) Prior Publication Data

US 2005/0181496 A1 Aug. 18, 2005

Related U.S. Application Data

(60) Provisional application No. 60/365,903, filed on Mar. 19, 2002.

(51) Int. Cl.
*A61K 31/44* (2006.01)
*C07D 309/00* (2006.01)

(52) U.S. Cl. .................. 514/336; 514/460; 514/473; 549/273

(58) Field of Classification Search ................ 549/273; 514/336, 460, 473
See application file for complete search history.

(56) References Cited

U.S. PATENT DOCUMENTS 5,208,244 A * 5/1993 Weiss .................. 514/336

FOREIGN PATENT DOCUMENTS

WO 9824396 A2 6/1998
WO WO 98/24396 * 11/1998

OTHER PUBLICATIONS

Naruto et a J. Am. Chem. Soc. 107, pp. 5262-5270 (1985).*
Kinsy et al Am. J. Physiol. Renal Physiol 292, pp. 853-860 (2007).*
Ackermann et al, J. Biol. Chem. vol. 270 No. 1 pp. 445-450 (1995).*
Feitsma et al, Pharm. Week. Sci. Ed. vol. 10 (1988) pp. 1-11.*
Gilabert et al, Analy. Chim. Acta (2002) pp. 319-335.*
Porter, Pure. & Appl. Chem. vol. 63, No. 8, pp. 1119-1122 (1991).*
Ackermann et al., "Inhibition of Macrophage Ca2+-Independent Phospholipase A2 by Bromoenol Lactone and Trifluoromethyl Ketones," J. Biol. Chem., 270(1):445-450 (1995).

(Continued)

*Primary Examiner*—Janet L. Andres
*Assistant Examiner*—Raymond Covington
(74) *Attorney, Agent, or Firm*—Armstrong Teasdale LLP

(57) ABSTRACT

A process for resolution of racemic BEL into its individual enantiomeric constituents by chiral HPLC. A method for determining the role of specific isoforms of $iPLA_2$ in biologic processes.

6 Claims, 9 Drawing Sheets

OTHER PUBLICATIONS

Feitsma et al., "Chromatographic Separation of Enantiomers," Pharmacy World & Science, 10(1):928-1231 (1988).

Gilbert et al., "Chromatographic Analysis of Lipoxygenase Products," Analytica Chimica Acta, 465:319-335 (2002).

Jenkins et al., "Identification of Calcium-Independent Phospholipase A2 (iPLA2) Beta, and Not iPLA2γ, as the Mediator of Arginine Vasopressin-induced Arachidonic Acid Release in A-10 Smooth Muscle Cells," J. Biol. Chem., 277(36):32807-32814 (2002).

Kinsey et al., "Identification of Calcium-independent phospholipase A2γ in Mitochondria and its Role in Mitochondrial Oxidative Stress," Am. J. Physiol. Renal. Physiol., 292:F853-F860 (2007).

Porter, "Resolution of Chiral Drugs," Pure & Appl. Chem., 63(8):1119-1112 (1991).

Gross, "Activation of Calcium-independent Phospholipase A2 by Depletion of Internal Calcium Stores," Biochem. Soc. Trans., 26:345-349 (1998).

Ma et al., "The Molecular Biology of the Group VIA Ca2+-Independent Phospholipase A2," Prog. Nucleic Acid Res. Mol. Biol., 67:1-33 (2001).

Miyake et al., "Multiple Phospholipase A2 Activities in Canine Vascular Smooth Muscle," Biochimica et Biophysica Acta, 1165:167-176 (1992).

Gross et al., "Rat and Human Pancreatic Islet Cells Contain a Calcium Ion Independent Phospholipase A2 Activity Selective for Hydrolysis of Arachidonate Which is Stimulated by Adenosine Triphosphate and is Specifically Localized to Islet Beta-Cells," Biochemistry, 32(1):327-336 (1993).

Ramanadham et al., "Characterization of an ATP-Stimulatable Ca2+-Independent Phospholipase A2 from Clonal Insulin-Secreting HIT Cells and Rat Pancreatic Islets: A Possible Molecular Component of the Beta-Cell Fuel Sensor," Biochemistry, 33(23):7442-7452 (1994).

McHowat et al., "Calcium-Independent Phospholipase A2 in Isolated Rabbit Ventricular Myocytes," Lipids, 33(12):1203-1212 (1998).

Wolf et al., "Long-Term Potentiation Requires Activation of Calcium-Independent Phospholipase A2," FEBS Letters, 377:358-362 (1995).

Gross et al., "Nitric Oxide Activates the Glucose-dependent Mobilization of Arachidonic Acid in a Macrophage-like Cell Line (RAW 264.7) That is Largely Mediated by Calcium-independent Phospholipase A2," J. Biol. Chem., 270(25):14855-14858 (1995).

Murakami et al., "Functional Coupling Between Various Phospholipase A2s and Cyclooxygenases in Immediate and Delayed Prostanoid Biosynthetic Pathways," J. Biol. Chem., 274(5):3103-3115 (1999).

Akiba et al., "Involvement of Group VI Ca2+-independent Phospholipase A2 in Protein Kinase C-dependent Arachidonic Acid Liberation in Zymosan-stimulated Macrophage-like P388D1 Cells," J. Biol Chem., 274(28):19906-19912 (1999).

Tran et al., "The Assembly of Very Low Density Lipoproteins in Rat Hepatoma McA-RH7777 Cells is Inhibited by Phospholipase A2 Antagonists," J. Biol. Chem., 275(32):25023-25030 (2000).

Alzola et al., "Activation by P2X7 Agonists of Two Phospholipases A2 (PLA2) in Ductal Cells of Rat Submandibular Gland," J. Biol. Chem., 273(46):30208-30217 (1998).

McHowat et al., "Endothelial Cell PAF Synthesis Following Thrombin Stimulation Utilizes Ca2+-Independent Phospholipase A2," Biochemistry, 40(49):14921-14931 (2001).

Ma et al., "Pancreatic Islets Express a Ca2+-Independent Phospholipase A2 Enzyme That Contains a Repeated Structural Motif Homologous to the Integral Membrane Protein Binding Domain of Ankyrin," J Biol. Chem., 272(17): 11118-11127 (1997).

Hazen et al., "Suicide Inhibition of Canine Myocardial Cytosolic Calcium-independent Phospholipase A2," J. Biol. Chem., 266(11):7227-7232 (1991).

Balsinde et al., "Bromenol Lactone Inhibits Magnesium-dependent Phosphatidate Phosphohydrolase and Blocks Triacylglycerol Biosynthesis in Mouse P388D1 Macrophages," J Biol. Chem., 271(50):31937-31941 (1996).

Balboa et al., "Involvement of Phosphatidate Phosphohydrolase in Arachidonic Acid Mobilization in Human Amnionic WISH Cells," J Biol. Chem., 273(13):7684-7690 (1998).

Baek et al., "Halo Enol Lactone Inhibitors of Chymotrypsin: Burst Kinetics and Enantioselectivity of Inactivation," Biochem. Biophys. Res. Comm., 178(3):1335-1342 (1991).

Dixon et al., "Acylation of the Enzymatic Site of δ-Chymotrypsin by Esters, Acid Anhydrides, and Acid Chlorides," J. Biol. Chem., 225:1049-1059 (1957).

Bligh et al., "A Rapid Method of Total Lipid Extraction and Purification," Canadian J. Biochem. Physiol., 37(8):911-917 (1959).

Ikegaki et al., "Glutaraldehyde Fixation of the Primary Antibody-Antigen Complex on Nitrocellulose Paper Increases the Overall Sensitivity of Immunoblot Assay," J. Immunol. Meth., 124:205-210 (1989).

Isenovic et al., "Role of Ca2+-Independent Phospholipase A2 in the Regulation of Inducible Nitric Oxide Synthase in Cardiac Myocytes," Hypertension, 35(2):249-254 (2000).

Daniels et al., "Haloenol Lactones," J. Biol. Chem., 258(24):15046-15053 (1983).

Chakravarty et al., "Haloenol Lactones: Enxyme-Activated Irreversible Inactivators for Serine Proteases," J. Biol. Chem., 257(2):610-612 (1982).

Daniels et al., "Halo Enol Lactones: Studies on the Mechanism of Inactivation of Alpha-Chymotrypsin," Biochem., 25(6):1436-1444 (1986).

Baek et al., "Alternate Substrate Inhibitors of an Alpha-Chymotrypsin: Enantioselective Interaction of Aryl-Substituted Enol Lactones," Biochem., 29(18):4305-4311 (1990).

Lin et al., "Cytosolic Phospholipase A2 is Coupled to Hormonally Regulated Release of Arachidonic Acid," Proc. Natl. Acad. Sci. USA, 89:6147-6151 (1992).

Qui et al., "Protein Kinase C-dependent and -independent Pathways of Mitogen-activated Protein Kinase Activation in Macrophages by Stimuli that Activate Phospholipase A2," J. Biol. Chem., 269(30):19480-19487 (1994).

Qui et al., "The Role of Calcium and Phosphorylation of Cytosolic Phospholipase A2 in Regulating Arachidonic Acid Release in Macrophages," J. Biol. Chem., 273(14):8203-8211 (1998).

Olivero et al., "Role of Protein Phosphorylation in Activation of Phospholipase A2 by the Polychlorinated Biphenyl Mixture Aroclor 1242," Toxicol. Appl. Pharm., 163:9-16 (2000).

Waggoner et al., "Structural Organization of Mammalian Lipid Phosphate Phosphatases: Implications for Signal Transduction," Biochim. Biophys. Acta, 1439:299-316 (1999).

Nanjundan et al., "Pulmonary Lipid Phosphate Phosphohydrolase in Plasma Membrane Signalling Platforms," Biochem. J., 358:637-646 (2001).

Hooks et al., "Lysophosphatidic Acid-Induced Mitogenesis is Regulated by Lipid Phosphate Phosphatases and is Edg-receptor Independent," J. Biol. Chem., 276(7):4611-4621 (2001).

Ramanadham et al., "Studies of the Role of Group VI Phospholipase A2 in Fatty Acid Incorporation, Phospholipid Remodeling, Lysophosphatidylcholine Generation, and Secretagogue-induced Arachidonic Acid Release in Pancreatic Islets and Insulinoma Cells," J. Biol. Chem., 274(20):13915-13927 (1999).

Channon et al., "A Calcium-dependent Mechanism for Associating a Soluble Arachidonoyl-hydrolyzing Phospholipase A2 with Membrane in the Macrophage Cell Line RAW 264.7," J. Biol. Chem., 265(10):5409-5413 (1990).

Glover et al., "Translocation of the 85-kDa Phospholipase A2 from Cytosol to the Nuclear Envelope in Rat Basophilic Leukemia Cells Stimulated with Calcium Ionophore or IgE/Antigen," J. Biol. Chem., 270(25):15359-15367 (1995).

Hirabayshi et al., "Critical Duration of Intracellular Ca2+ Response Required for Continuous Translocation and Activation of Cytosolic Phospholipase A2," J. Biol. Chem., 274(8):5163-5169 (1999).

Takuma et al., "Role of Ca2+-Independent Phospholipase A2 in Exocytosis of Amylase from Parotid Acinar Cells," J. Biochem., 121:1018-1024 (1997).

Naruto et al., "Analysis of the Interaction of Haloenol Lactone Suicide Substrates with alpha-Chymotrypsin Using Computer Graphics and Molecular Mechanics," J. Am. Chem. Soc., 107(18):5262-5270 (1985).

Wolf et al., "Identification of Neutral Active Phospholipase C Which Hydrolyzes Choline Glycerophospholipids and Plasmalogen Selective Phospholipase A2 in Canine Myocardium," Journal of Biological Chemistry, 260(12):7295-7303 (1985).

Lehman et al., "Arachidonic Acid Release from Aortic Smooth Muscle Cells Induced by [Arg8]Vasopressin is Largely Mediated by Calcium-independent Phospholipase A2," Journal of Biological Chemistry, 268(28):20713-20716 (1993).

McHowat et al., "Selective Hydrolysis of Plasmalogen Phospholipids by Ca2+-Independent PLA2 in Hypoxic Ventricular Myocytes," American J. Physiol Cell Physiol., 274(6):C1727-C1737 (1998).

Atsumi et al., "Fas-induced Arachidonic Acid Release Is Mediated by Ca2+-independent Phospholipase A2 but Not Cytosolic Phospholipase A2, Which Undergoes Proteolytic Inactivation," Journal of Biological Chemistry, 273(22):13870-13877 (1998).

Roshak et al., "Human Calcium-independent Phospholipase A2 Mediates Lymphocyte Proliferation," Journal of Biological Chemistry, 275(46):35692-35698 (2000).

Atsumi et al., "Distinct Roles of Two Intracellular Phospholipase A2s in Fatty Acid Release in the Cell Death Pathway," Journal of Biological Chemistry, 275(24):18248-18258 (2000).

Andrews et al., "Characterization of the Lipid Acyl Hydrolase Activity of the Major Potato (Solanum tuberosum) Tuber Protein, Patatin, by Cloning and Abundant Expression in a baculovirus Vector," Biochem. J., 252:199-206 (1988).

Tang et al., "A Novel Cytosolic Calcium-independent Phospholipase A2 Contains Eight Ankyrin Motifs," Journal of Biological Chemistry, 272(13):8567-8575 (1997).

Mancuso et al., "The Genomic Organization Complete mRNA Sequence, Cloning, and Expression of a Novel Human Intracellular Membrane-associated Calcium-independent Phospholipase A2," Journal of Biological Chemistry, 275(14):9937-9945 (2000).

Jenkins et al., "Identification of the Calmodulin-binding Domain of Recombinant Calcium-independent Phospholipase A2B," Journal of Biological Chemistry, 276(10):7129-7135 (2001).

Wolf et al., "The Calcium-dependent Association and Functional Coupling of Calmodulin with Myocardial Phospholipase A2," Journal of Biological Chemistry, 271(35):20989-20992 (1996).

Wolf et al., "Depletion of Intracellular Calcium Stores Activates Smooth Muscle Cell Calcium-independent Phospholipase A2," Journal of Biological Chemistry, 272(3):1522-1526 (1997).

Nowatzke et al., " Mass Spectrometric Evidence That Agents That Cause Loss of Ca2+ from Intracellular Compartments Induce Hydrolysis of Arachidonic Acid from Pancreatic Islet Membrane Phospholipids by a Mechanism That Does Not Require a Rise in Cytosolic Ca2+ Concentration," Endocrinology, 139(10):4073-4085 (1998).

Zupan et al., "Structural Determinants of Haloenol Lactone-Mediated Suicide Inhibition of Canine Myocardial Calcium-Independent Phospholipase A2," J. Med. Chem., 36(1):95-100 (1993).

Wolf et al., "Expression, Purification, and Kinetic Characterization of a Recombinant 80-kDa Intracellular Calcium-independent independent Phospholipase A2," Journal of Biological Chemistry, 271(48):30879-30885 (1996).

Laemmli, "Cleavage of Structural Proteins During the Assembly of the Head of Bacteriophage T4," Nature, 227(5259):680-685 (1970).

International Search Report for PCT Application No. PCT/US03/08834, dated Dec. 1, 2003.

Farooqui et al., "Phospholipase A2 and Its Role in Brain Tissue," Journal of Neurochemistry, 69:889-907 (1997).

* cited by examiner

PKCα

PKCδ

PKCε

PKCι

| AVP | − | + | + | − | + | + | − | + | + |
| (S)-BEL | − | − | + | − | − | + | − | − | + |

US 7,741,344 B2

PROCESS FOR PREPARING PURIFIED S-BEL AND R-BEL AND COMPOSITIONS THEREOF

CROSS REFERENCE TO RELATED APPLICATIONS

This application claims the benefit of priority of U.S. Provisional Patent Application 60/365,903 filed Mar. 19, 2002 and claims the benefit of priority to the PCT International Application Ser. No. PCT/US03/08834 filed Mar. 19, 2003 which is incorporated in its entirety by reference.

FIELD OF THE INVENTION

This invention relates to a process for the preparation of enantiomerically pure and optically enriched S-BEL from a composition comprising enantiomers S-BEL and R-BEL using HPLC chiral chromatography. More particularly, this invention relates to a process for preparing optically active purified S-BEL and a composition comprising purified S-BEL. This invention also relates to a process for preparing purified R-BEL and a composition comprising purified R-BEL. This invention also relates to a process for selective inhibition of iPLA$_2$ lipases. More particularly this invention relates to a process for selective inhibition of lipases which perform functions in cells.

BACKGROUND OF THE INVENTION

Calcium-independent phospholipases A2 (iPLA$_2$s) constitute an important group of intracellular enzymes which function to hydrolyze esterified fatty acids from membrane phospholipids in response to agonist stimulation, changes in intracellular calcium ion homeostasis, and alterations in cellular energy requirements (for reviews, see 1-3). In early studies, we and others demonstrated that the majority of PLA$_2$ activity in most non-circulating mammalian cell types including smooth muscle cells (4), pancreatic jβ-cells (5,6), cardiomyocytes (7,8), and hippocampal neurons (9) was calcium-independent and inhibited by racemic (E)-6-(bromomethylene)-3-(1-naphthalenyl)-2H-tetrahydropyran-2-one (rac-BEL). Based upon activity assays, calcium requirements, loss of arachidonylated phospholipid mass, and inhibition of iPLA$_2$ by rac-BEL (R-BEL), a diverse array of cellular processes has been proposed to be regulated by iPLA$_2$s, including arachidonic acid (AA) release (10-15), cellular proliferation (16), assembly of VLDL (17), putinergic receptor-stimulated kallikrein secretion (18), apoptosis (19), endothelial cell PAF synthesis (20), and induction of iNOS and nitric oxide production (21).

Three distinct subclasses of iPLA$_2$ have been identified at the genetic level (with subsequent confirmation of iPLA$_2$ catalytic activity by recombinant technologies) and have been designated iPLA$_2$α, iPLA$_2$β, and iPLA$_2$γ, in order of their discovery (22-24). The iPLA$_2$s have been categorized based upon their strict conservation of nucleotide-binding (GXGXXG) and lipase (GXSTG) consensus sequences (FIG. 1). Two of the iPLA$_2$ subclasses, iPLA$_2$β and iPLA$_2$γ, have been cloned from mammalian cDNA libraries while the ortholog of iPLA$_2$α (patatin), at the time of this writing (with 98.7% of tire human genome sequenced), has not been identified in mammals. Calcium-independent phospholipase A$_2$β contains eight ankyrin-repeat domains which are believed to facilitate intracellular sorting (23, 25, 26) and a CaM-binding domain near the C-terminus which binds calcium-activated CaM and regulates enzyme activity (27) (FIG. 1). The binding of CaM to iPLA$_2$β results in inhibition of iPLA$_2$β activity which is reversible through removal of Ca$^{+2}$ and subsequent dissociation of CaM from the C-terminus of iPLA$_2$β (27, 28). In this paradigm, iPLA$_2$β is regulated through alterations in cellular calcium ion homeostasis and becomes activated after dissociation from its complex with Ca$^{+2}$/CaM when intracellular calcium stores are depleted by SERCA inhibitors, calcium-ionophores, or agonist stimulation (29, 30). In contrast, the recently identified iPLA$_2$γ does not bind CaM and its mechanisms of regulation are unknown at present.

Studies of iPLA$_2$ have utilized the mechanism-based suicide inhibitor rac-BEL as a pharmacologic tool to identify the type of intracellular phospholipase A$_2$ involved in many diverse cellular processes. Since rac-BEL inhibits both iPLA$_2$β and iPLA$_2$γ at low microflora concentrations (24, 25, 31, 32), it is impossible to assign rac-BEL-mediated inhibition of AA release to iPLA$_2$β or iPLA$_2$γ activities. Accordingly, it became necessary to develop pharmacologic approaches which could discriminate between iPLA$_2$β and iPLA$_2$γ to facilitate identification of their biologic roles. In addition, it has been reported in the Journal (33, 34) that high concentrations of BEL (25 μM) partially inhibit the magnesium-dependent cytozoic phosphatidate phosphohydrolase, PAP-1, which converts phosphatidic acid to diacylglycerol (DAG). In those investigations, it was proposed that PAP-1 inhibition by BEL would prevent activation of protein kinase C leading to attenuated AA release. However, "rescue" experiments in which PKC was exogenously activated by phorbol esters or diacyl glycerol analogs after BEL treatment were not reported by the authors to address their hypothesis (33, 34).

BRIEF DESCRIPTION OF INVENTION

In an aspect, a process for preparing S-BEL and R-BEL comprises passing a racemic mixture comprising S-BEL and R-BEL through at least one chromatographic column packed with an optical resolution packing material to optically resolve S-BEL from the racemic mixture. In an aspect the packing material comprises a silica.

In an aspect a method of separating a racemic composition comprising R-BEL and S-BEL into purified R-BEL and S-BEL respectively comprises passing a racemic composition comprising R-BEL and S-BEL through an HPLC chiral separation column which comprises a stationary phase and eluting said R-BEL and said S-BEL from said column.

In an aspect a process for chromatographically resolving enantiomerically pure or optically enriched BEL from a mixture containing two enantiomers of BEL using chiral chromatography comprises a liquid mobile phase and a chiral stationary phase.

In an aspect the solid chiral stationary phase is attached to a silica or silica.

In an aspect, the inventors have shown the identification of iPLA$_2$β and not iPLA$_2$γ, as the Mediator of AVP-induced Arachidonic Acid Release in A-10 Smooth Muscle Cells by enantioselective Mechanism-Based Discrimination of intracellular lipases.

In an aspect, an isolated and purified S-BEL.
In an aspect, an isolated and purified R-BEL.
In an aspect, a purified composition comprising R-BEL.
In an aspect, a purified composition comprising S-BEL.
In an aspect, a method of identifying whether a lipase enzyme is metabolically active in a cellular environment comprises contacting said cellular environment with at least one of S-BEL and R-BEL and determining the identity of the lipase based on the interaction of said lipase with at least one of S-BEL and R-BEL.

In an aspect, a diagnostic method for determining the metabolic activity of a lipase in a cellular environment comprises contacting said cellular environment with at least one of S-BEL and R-BEL and determining the identity of the lipase based on the interaction of said lipase with at least one of S-BEL and R-BEL.

In an aspect, a diagnostic kit/method for determining the metabolic activity of a lipase in a cellular environment comprises providing a cellular environment comprising a lipase for which it is desired to determine the metabolic activity, contacting said cellular environment with at least one of S-BEL and R-BEL and determining the identify and/or activity of the lipase based on the interaction of said lipase with at least one of S-BEL and R-BEL.

In an aspect, a method of identifying whether a lipase enzyme is metabolically active in a cellular environment comprises contacting said cellular environment with at least one of S-BEL and R-BEL and determining the identify of the lipase based on the interaction of said lipase with S-BEL.

In an aspect, a method of identifying whether a lipase enzyme is metabolically active in a cellular environment comprises contacting said cellular environment with at least one of S-BEL and R-BEL and determining the identity of the lipase based on the interaction of said lipase with R-BEL.

In an aspect, a method of inactivating a lipase enzyme which is metabolically active in a cellular environment comprises contacting said cellular environment with at least one of S-BEL and R-BEL and thereby rendering the lipase inactive.

In an aspect, a method of selectively inhibiting iPLA2γ in a composition comprises effectively contacting the same with an effective inhibiting amount of S-BEL.

In an aspect, a method for pharmacologically distinguishing iPLA2γ from iPLA2β comprises contacting a candidate iPLA2 with S-BEL and if the selectivity is high of S-BEL to the candidate iPLA₂, then determining that the iPLA2 is iPLA2γ. As used herein, the term "candidate" includes members of the iPLA2 family.

In an aspect, a method of differentially inhibiting iPLA2γ and iPLA2β comprises contacting the same with S-BEL, observing selectivity of S-BEL toward iPLA2γ or iPLAαβ and determining that said iPLA2β has been inhibited. In an aspect, iPLA$_2$β is selectively inhibited.

In an aspect, a method for identifying/determining whether iPLA$_2$β or iPLA$_2$γ is active in a metabolic pathway or chemical process believed to utilize iPLA$_2$ enzymes comprises contacting said pathway or process with at least one of R-BEL and S-BEL, determining if said R-BEL or S-BEL has an inhibiting effect and further determining whether this effect is on iPLA$_2$γ or iPLA$_2$β, identifying iPLA$_2$β or iPLA$_2$γ as active.

In an aspect a S-BEL inhibited iPLA$_2$γ is provided.
In another aspect an R-BEL inhibited iPLA$_2$γ is provided.

DETAILED DESCRIPTION OF THE INVENTION

Figure 1:
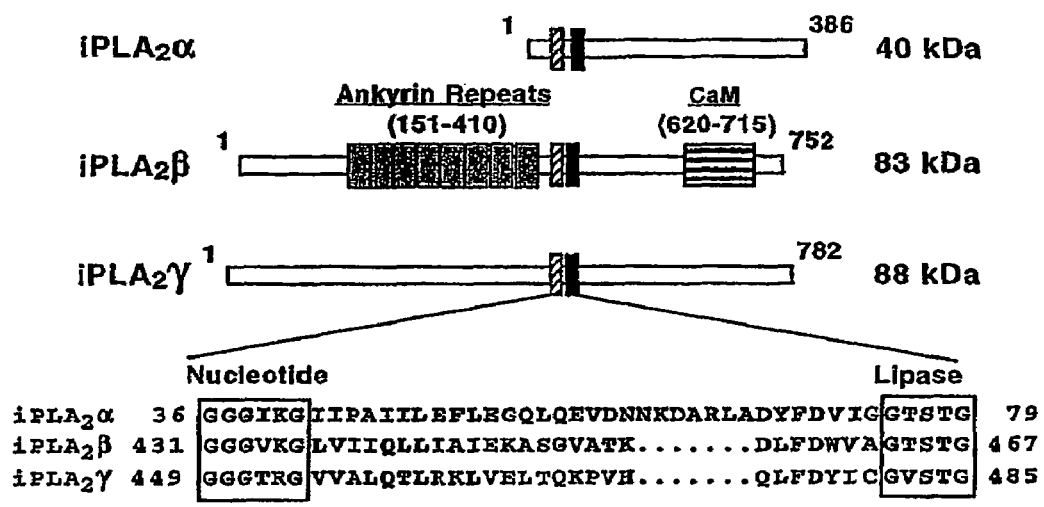
FIG. 1 depicts the calcium-independent phospholipase A$_2$ (iPLA$_2$) gene family and sequence alignment of iPLA2 nucleotide and lipase consensus motifs.

In an aspect, the inventors employed rac-BEL to demonstrate a 1000 fold selectivity iPLA$_2$ vs. cPLA$_2$ and SPLA$_2$ family members (31, 32). In a further aspect, based upon the increasing appreciation of the utility of chiral pharmacologic agents in enhancing the specificity of inhibitors toward targeted biologic processes, we discovered that (R)- and (S)- BEL differentially inhibits iPLA$_2$β and iPLA$_2$γ activities. Moreover, we discovered that development of chiral mechanism-based inhibitors provides an increased degree of discrimination between specific targeted enzyme systems and those of "non-specific inhibition. We exploited the resolution of racemic BEL into its individual enantiomeric constituents by chiral HPLC. We showed the selective inhibition of iPLA$_2$β by (S)-BEL and iPLA$_2$γ by (R)-BEL, and demonstrated that BEL-mediated inhibition of AA release in A-10 cells is likely mediated by iPLA$_2$β and not due to inhibition of iPLA$_{2γ}$ or the effects of BEL on MAPK or PKC activation.

Agonist-stimulated release of arachidonic acid (AA) from cellular phospholipids in many cell types (e.g. myocytes, β-cells, and neurons) has been demonstrated to be primarily mediated by calcium-independent phospholipases A2 (iPLA$_2$s) which are inhibited by the mechanism-based inhibitor (E)-6-(bromomethylene)-3-(1-naphthalenyl)-2H-tetrahydropyran-2-one (BEL).

As used herein, the terms "preparative HPLC" and "HPLC" include a HPLC (high performance liquid chromatography) process for the isolation and purification of compounds including compounds such as S-BEL and R-BEL. (see www.pharm.uky.edu/ASRG/HPLC/hplcmytry.html)

In an aspect, chemical separation is brought about by utilizing our discovery that S-BEL and R-BEL have different migration rates given a selected chiral chromatographic column and mobile phase employed therewith.

The separation of enantiomers such as S-BEL and R-BEL by means of liquid chromatography (LC) using chiral stationary phases is based on the reversible diasteromeric association between the chiral environment in the column and the enantiomers fed to the column.

In an aspect the column is a racemic resolveable and separable column.

Useful illustrative compositions to be separated and refined herein include racemic mixtures, including those comprising racemates. In an aspect a racemate is fed to a chiral chromatographic column producing one, two or multiple eluents respectively therefrom copying R-BEL and S-BEL respectively.

In an aspect a continuous chiral chromatrographic column is employed. In an aspect a batch or semi-continuous type chiral chromatrographic column is employed. In an aspect, the column is operably and suitably effectively configured to provide the desired separation, purification and elution.

As used herein, the term "purification" includes a process of separation or extracting a target or a designated compound(s) such an optical isomer(s) from other related compounds such as a related optical isomer, wherein each compound has a characteristic peak under chiral chromatographic conditions.

As used herein, the term "racemic" denotes the presence of equimolar or nearly equimolar amounts of dextrorotatory and levorotatory enantiomers of a compound.

In an aspect S-BEL comprises S—(E)-6-(bromomethylene)-3-(1-naphthalenyl)-2H-tetrahydropyran-2-one and R-BEL comprises R—(E)-6-(bromomethylene)-3-(1-naphthalenyl)-2H-tetrahydropyran-2-one.

In an aspect a racemic composition of S-BEL and R-BEL is separated, refined or made nonracemic by using a suitable chiral chromatograph.

In an aspect a suitable chiral chromatograph is one which is enantiomer separable capable, i.e., can separate enantiomers.

In an aspect a racemic composition of BEL entantiomers are resolved providing one or multiple eluents comprising S-BEL and R-BEL respectively. In an aspect a racemic BEL composition is fed to a HPLC chiral chromatograph column to provide a chiral chromatograph product eluent comprising chiral chromatographic produced R-BEL and S-BEL In an aspect BEL entantiomers are resolved by HPLC utilizing a Chirex column of 3,5 dinitrobenzoyl-R-phenylglycine attached to a silica matrix as the stationary chiral phase.

In an aspect the column is calibrated.

In an aspect, the chiral column is equilibrated with hexane/dichloroethane/ethanol and optical enantiomers are eluted isocratically at a flow rate of 2 ml/min.

In an aspect isocratic elution is carried out in a process whereby the chromatographic procedure or separation in which the composition of the eluent is maintained constant or nearly constant.

In an aspect, elution of BEL compositions from the column is monitored by UV absorbance at 280 nm. Peaks corresponding to the R BEL and S BEL enantiomers were collected, dried under nitrogen and stored at −20° C.

In general the degree of separation or refinement is greater than about 60% (racemic) to about 90% and in the range from about 70% to about 85%.

Illustrative useful chiral HPLC columns include those which operate by immobilizing single enantiomers onto a stationary phase(s) in the column(s). Achieving capable and sufficient resolution depends to an extent on the effective formation of transient diastereoisomers on the surface of the column packing which in an aspect is the immobile phase. Generally the compound which forms the more stable diastereoisomer will be most or preferentially retained whereas the opposite enantiomer will form a less stable diastereoisomer will elute first. It is desired in this discovery to achieve a high degree of discrimination between enantiomers in passing through and effectively contacting the phases of the chiral HPLC chromatographic column to isolate and purified S-BEL and R-BEL. Useful illustrative operably configured chiral HPLC columns include those which operate effectively on the basis of chirality which is topical handedness or the property of nonidentity of an object with its mirror image.

In an aspect, the chromatography comprises a liquid mobile phase comprises 3,5-dinitrobenzoyl-(R)-phenylglycine attached to a silica matrix as a solid chiral stationary phase.

In an aspect, the eluetant comprises at least one of a purified and isolated S-BEL, a purified and isolated R-BEL, a composition comprising S-BEL and a composition comprising R-BEL.

As used herein, the terms "silica" and "silica based matrix" include any useful silicon oxide or silicon dioxide including silica gel, silica oxide, which is a colourless or white solid effectively used as the support or basis for chromatographic procedures. Generally in silica chromatographic processes, the silica is heated to above about 100C to drive off water. In an aspect silica material serves as a support.

Illustrative useful chiral stationary phases for use in chiral chromatography include those materials selected from the group consisting of Type I, II, III, IV and V CSP (chromatographic stationary phase) as classified by Irving Wainter (57).

Illustrative useful Type I CSP include those which differentiate enantiomers by formation of complexes based on attractive interactions which include hydrogen bonds, p-p interactions and dipole stacking.

Illustrative useful Type II CSPs include those which involve a combination of interactions and inclusion complexes to produce a separation, these are largely based on cellulose derivatives.

Illustrative useful Type III CSPs include those which rely on solute entering into chiral cavities to form inclusion complexes, such as the cyclodextrin type of column developed by Prof. D. W. Armstrong (58). Other useful CSPs include crown ethers and helical polymers such as polytriphenylmethyl methacrylate.

Illustrative useful Type IV CSP include those which separate by means of diastereomeric metal complexes which are known as Chiral ligand exchange chromatrograph (CLEC) and developed by Davankov (59, 60).

Illustrative useful chiral columns are also classified by chemical type. Illustrative useful chiral stationary phases include Brush type (Pirkle), cellulose, cyclcodextrin, macrocylic antibiotics, protein, ligand exchange and crown ethers.

These illustrative useful and other useful illustrative chiral columns include those listed in the Online Guide to Chiral HPLC by Mark Earl , see www.raell.demon.co.uk/chem/CHIbook/Chiral.htm.

A useful comprehensive guide to chiral HPLC applications is disclosed at www.chromtech.se/chiral.htm.

In an aspect this discovery is employed to provide an enhanced improved separation process for racemic compositions of S-BEL and R-BEL and provides a straightforward expeditious one step low cost method. This discovery is useful as a research tool to identify the role of lipases in biologic processes, and to probe active sites as by proteonomics. This discovery is also useful for proof of concept of specific isoformers used in lipase studies.

Recently, the family of mammalian iPLA$_2$s has been extended to include iPLA$_2\gamma$ which previously could not be pharmacologically distinguished from iPLA$_2\beta$.

To determine if iPLA$_2\beta$ or iPLA$_2\gamma$ (or both) were the enzymes responsible for arginine vasopressin (AVP)-induced AA release from A-10 cells, it became necessary to selectively inhibit iPLA$_2\beta$ and iPLA$_2\gamma$ in intact cells. Racemic BEL was separated into its enantiomeric constituents by chiral HPLC. Remarkably, (S)-BEL was approximately an order of magnitude more selective for iPLA$_2\beta$ in comparison to iPLA$_2\gamma$. Conversely, (R)-BEL was approximately an order of magnitude more selective for iPLA$_2\gamma$ than iPLA$_2\beta$. The AVP-induced liberation of AA from A-10 cells was selectively inhibited by (S)-BEL (IC$_{50}$ about 1 μM but not (R)-BEL, demonstrating that the overwhelming majority of AA release is due to iPLA$_2\beta$ and not iPLA$_2\gamma$ activity. Furthermore, pre-treatment of A-10 cells with (S)-BEL did not prevent AVP-induced MAPK phosphorylation or PKC translocation. Finally, two different cell-permeable protein kinase C activators (phorbol-12-myristate-13-acetate and 1,2-dioctanoyl-sn-glycerol) could not restore the ability of A-10 cells to release AA after exposure to (S)-BEL, thus supporting the downstream role of iPLA$_2\beta$ in AVP-induced AA release.

This discovery has multiple utilities and illustratively is useful for proof of concept of specific isoformers used in lipase studies, for tagging iPLA$_2$ family members and labelling molecules. In an aspect this discovery is useful as one or more research tools, diagnostic method(s) and tool for selective inhibition of iPLA$_2$ family members such as targeted disease states, mode of action studies and investigative methods.

The following examples are described in detail in order to facilitate a clear understanding of the invention. It should be understood, however, that the detailed expositions of the application of the invention, are given by way of illustration only and are not to be construed as limiting the invention since various changes and modifications within the spirit of the invention will become apparent to those skilled in the art from this detailed description.

EXAMPLES

Experimental Procedures—Materials—BEL, phorbol myristate 13-acetate (PMA), and 1,2-Dioctanoyl-sn-glycerol (DOG) were obtained from Calbiochem. A Chirex HPLC column comprised of a stationary phase of (R)-phenylglycine linked through an amide linkage to 3,5-dinitrobenzoic acid was purchased from Phenomenex. Three-fold-crystallized chymotrypsin, N-succinyl-Ala-Ala-Pro-Phe-7-amido-4-methylcoumarin, fatty acid free bovine serum albumin (low endotoxin), antibodies against PKCα, and most other reagents were obtained from Sigma. AVP was purchased from Bachem. HPLC-grade organic solvents and channeled LK6D Silica Gel 60 Å thin layer chromatography plates (Whatman) were obtained from Fisher Scientific. Enhanced chemiluminescence (ECL) reagents and film were purchased from Amersham Pharmacia L-α-1-palmitoyl-2-[1-$^{14}$C]-arachidonyl-phosphatidylcholine, L-α-1-palmitoyl-2-[1-$^{14}$C]-oleoyl-phosphatidylcholine, [5,6,8,9,11,12,14,15-$^3$H(N)]-arachidonic acid, and L-α-dipalmitoyl [glycerol-$^{14}$C(U)]-phosphatidic acid were purchased from NEN. A-10 cells derived from rat aortic smooth muscle were obtained from the ATCC and cultured as described previously (10). (R) and (S) enantiomers of (E)-6-(iodomethylene)-3-(1-naphthalenyl)-2H-tetrahydropyran-2-one (αNpI6) were received (Univ. of Illinois, Urbana). Anti-Active MAPK (pTEpY) and Anti ERK ½ antibodies were obtained from Promega. Antibodies against PKCε and PKCδ were received (St. Louis Univ., St. Louis). Antibodies against PKC$_1$ were obtained from BD Transduction Laboratories.

Recombinant iPLA$_2$ Enzymes—Recombinant iPLA$_2\beta$ was expressed and purified from Sf9 cells as previously described (35). Recombinant full-length iPLA$_2\gamma$ was expressed in Sf9 cells and the membrane fraction was washed and isolated as previously described (24).

Separation of BEL Enantiomers—BEL enantiomers were resolved by HPLC utilizing a Chirex column of 3,5-dinitrobenzoyl-(R)-phenylglycine attached to a silica matrix as a stationary chiral phase. The chiral column was equilibrated with hexane/dichloroethane/ethanol (150/15/1) and optical enantiomers were eluted isocratically at a flow rate of 2 ml/min. Elution of BEL compositions from the column was monitored by UV absorbance at 280 nm. Peaks corresponding to the (R)- and (S)-enantiomers were collected, dried under N$_2$, and stored at M-1-20° C. The concentration of BEL for each experiment was determined spectrophotometrically based on UV absorbance ($\epsilon_{280}$=6130 cm$^{-1}$ M-1) in acetonitrile. This shows the separation at preparation of S-BEL and R-BEL respectively by our discovery.

Inhibition of α-Chymotrypsin by BEL—The kinetics of α-chymotrrpsin inactivation by (R)-, (S)-, and rac-BEL were performed similar to methods previously described (36). The concentration of α-chymotrypsin (MW=25,000) was determined using an A$^{1\%}$=20 (1 cm pathlength) at 280 nm (37). Briefly, one milliliter of α-chymotrypsin (2 μM) was incubated with up to a 5-fold molar excess of (R)-,(S)-, or rac-BEL dissolved in acetonitrile or vehicle alone for 5 mm at 22° C. in 0.1 M sodium phosphate buffer, pH 7.2. A-10 μl aliquot of the reaction was diluted 1000-fold in 10 mL of 0.1 sodium phosphate buffer, pH 7.2 containing 100 mM hydrazine to deacylate transiently-inactive BEL-chymotrypsin complexes. Following incubation at 22° C. for 1 hr, chymotrypsin activity in each diluted sample was measured utilizing a SPECTRAmax GeminiXS microplate spectrofluorometer with N-succinyl-Ala-Ala-Pro-Phe-7-amidomethylcoumarin (50 μM) as substrate for 1 mm at 25° C. Excitation and emission wavelengths were 380 nm and 460 nm, respectively.

Assay of iPLA$_2\beta$ and iPLA$_2\gamma$ Inhibition by BEL—Purified recombinant iPLA$_2\beta$ or Sf9 cell membranes containing recombinant iPLA$_2\gamma$ were incubated with (R) BEL, (S) BEL, racemic BEL, or ethanol vehicle for 3 mm at 22° C. in the presence of 100 mM Tris-HCl (pH 7.0) and 4 mM EGTA (for iPLA$_2\beta$) or 100 mM Tris-acetate (pH 8.0) and 4 mM EGTA (for iPLA$_2\gamma$). The concentration of BEL used for each test ranged from 0 to 16 μM. L-α-1-palmitoyl-2-[1$^{14}$C]-arachidonyl-phosphatidylcholine (5 μM final concentration) or L-α-1-palmitoyl-2-[1-$^{14}$C]-oleoyl-phosphatidylcholine (5 μM final concentration) in ethanol was then added to each sample and incubated at 37° C. for 2 min. Reactions were terminated by extraction of radiolabeled products into butanol, and reactants and products were separated by thin layer chromatography using Whatman LK6D 60 Å Silica Gel plates with petroleum ether/ethyl ether/acetic acid (70:30:1) as the mobile phase. Regions corresponding to the migration of a fatty acid standard visualized by iodine staining were scraped into vials and radioactivity was quantified by scintillation spectrometry.

Quantification of [$^3$H]-Arachidonic Acid Liberation from A-10 Phospholipids—Rat aortic smooth muscle A-10 cells, cultured in 60 mm dishes (2.5×10$^5$ cells/dish), were radiolabeled with 0.5 μCi [$^3$H]-arachidonic acid per dish as previously described (29). Cells were washed once with DMEM containing 0.25% fatty acid free bovine serum albumin followed by two washes with DMEM alone. Cells were then incubated with the indicated concentrations of (R)-, (S)-, rac-BEL, or ethanol vehicle (0.1% final concentration) in DMEM for 20 min. This media was removed and the cells were then incubated with DMEM containing 10% heat-inactivated fetal bovine serum in the absence or presence of 1 μM AVP. In some tests, PMA (1 μM) or DOG (10 μM) was added to the medium containing AVP. After 5 mm, 1 ml of this medium was removed, lipids were extracted into 2 ml of chloroform/methanol/acetic acid (25:24:1 v/v) (38), and the remaining cells were scraped into 1 ml of deionized water prior to lipid extraction as described above. The chloroform layer was evaporated under nitrogen and the extracted lipids were separated by thin layer chromatography (petroleum ether/ethyl ether/glacial acetic acid 70:30:1). Regions containing fatty acids and phospholipids were scraped into vials and radioactivity was quantified by liquid scintillation spectrometry.

Measurement of Cytosolic and Membrane-bound Phosphatidate Phosphohydrolase Activities—A-10 cells were grown to confluency, washed twice in ice-cold phosphate-buffered saline, and harvested in lysis buffer (50 mM Tris-HCl, pH 7.4 containing 0.25 M sucrose and 0.2 mM DTT). After brief sonication utilizing a Vibra-Cell VC4O sonicator (5×1 s pulses at 30% power), the lysed cell suspension was centrifuged at 100,000×g for 1 hr to separate cytosolic and membrane fractions. In some tests, A-10 cells were washed and pretreated with BEL or ethanol vehicle (as described above for tests examining [$^3$H]-AA liberation) before isolation of cell homogenates. Each fraction (40 μL) was pre-incubated with BEL (up to 100 μM) or ethanol vehicle at 22° C. for 5 mm in the presence of 50 mM Tris-HCl, pH 7.2 containing 10 mM β-mercaptoethanol, 2 mM $MgCl_2$, and 1 mM EGTA (90 μL final volume). Dipaimitoyl phosphatidic acid (100 μM final concentration containing 0.05 μCi L-α-dipalmitoyl [glycerol-$^{14}$C(U)]-phosphatidic acid per reaction in the presence of 1 mM Triton X-100) was added to each reaction and incubated at 37° C. for 5-10 mm. Reactions were terminated with 900 μL of 5% acetic acid and extracted into chloroform by the method of Bligh and Dyer (38) prior to separating dipaliitoyl glycerol by TLC utilizing chloroform: methanol: water (65:35:2) as the mobile phase prior to quantification by scintillation spectrometry.

Determination of Phosphorylated MAPK—Confluent A-10 cells in 10 cm dishes were incubated overnight in the presence of DMEM containing 1% fetal bovine serum to reduce background phosphorylation of ERK1 and ERK2. Cells were washed twice with DMEM without serum and pre-incubated with 5 μM (R)-BEL, (S)-BEL, rac-BEL, or ethanol vehicle in DMEM without serum for 15 mm at 37° C. This media was then removed and the cells were incubated with 1 μM AVP for 5 mm, at 37° C. After washing once with ice-cold phosphate-buffered saline (PBS), cells were scraped into RIPA buffer (PBS, pH 7.4 containing 1% Igepal CA-630, 0.5% sodium deoxycholate, 0.1% SDS, 0.5 mM 4-(2-aminoethyl) benzenesulfonylfluoride, 10 μg/ml aprotinin, and 1 mM sodium orthovanadate), incubated on ice for 30 mm, and then centrifuged at 10,000×g for 10 mm. The protein concentrations of the sample supernatants were determined utilizing the bicinchoninic acid (BCA) assay (Pierce) with bovine serum albumin (BSA) as a standard. Samples were electrophoresed according to the method of Laemmli (39) and transferred to a PVDF membrane by electroelution in 10 mM CAPS (pH 11) for ECL Western analysis. After blocking with Tris-buffered saline containing 0.1% Tween-20 (TBS-T) and 5% non-fat dry milk for 2 hrs, primary rabbit polyclonal antibodies against phosphorylated (pTEpY) and dephosphorylated MAPK diluted 1:5000 in PBS containing 5% BSA were incubated with the blot for 1 hr. After washing with TBS-T, the blots were incubated with ice-cold PBS containing 0.25% glutaraldehyde for 15 mm as previously described (40), washed, and incubated with a protein A-peroxidase conjugate diluted (1:5000) in TBS-T containing 5% BSA for 1 hr. bimunoreactive bands were visualized by ECL as described by the manufacturer (Amersham Pharmacia).

Determination of PKC Translocation—Confluent A-10 cells in 10 cm dishes were washed twice with DMEM without serum, followed by incubation with either 5 μM (S)-BEL or ethanol vehicle in DMEM for 15 min at 37° C. This media was then removed and DMEM with or without 1 μM AVP was incubated with the cells for 5 min. After washing with ice-cold PBS, the cells were collected by scraping into 20 mM Tris-HCl, pH 7.4 containing 0.33 M sucrose, 5 mM EDTA, 0.5 mM 4(2-aminoethyl)benzenesulfonylfluoride, and 5 μg/ml leupeptin and were lysed by three cycles of flash freezing with liquid nitrogen and thawing. Each sample was then further homogenized utilizing a teflon homogenizer before isolating the low speed pellet (1,000×g), membrane (100,000×g pellet), and cytosol (100,000×g supernatant) fractions. The protein concentrations of the fractions were determined utilizing the bicinchoninic acid (BCA) assay (Pierce) with BSA as a standard. Samples were electrophoresed and subjected to ECL Western analysis utilizing rabbit polyclonal antibodies against PKCα and PKCε as described above for MAPK phosphorylation. For blots incubated with mouse monoclonal antibodies against PKCδ and PKCι., an anti-mouse IgG (Fab specific)-peroxidase conjugate was utilized in place of the protein A-peroxidase conjugate.

Figure 2:
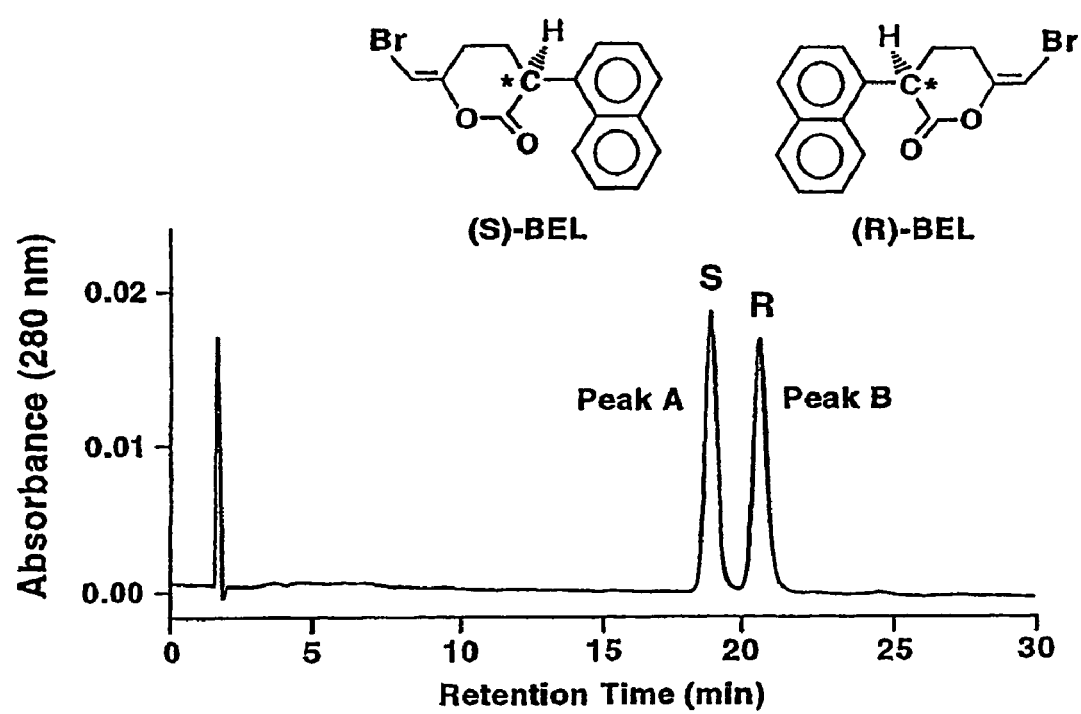
FIG. 2 depicts separation of BEL enantiomers by chiral HPLC.

Results—Separation of BEL Enantiomers—Since BEL contains a chiral center at the C-2 position (FIG. 2), (R)-BEL and (S)-BEL might have different potencies and/or selectivities for $iPLA_2\beta$ and $iPLA_2\gamma$ so that individual enantiomers of BEL could be exploited to identify the roles of $iPLA_2\beta$ and $iPLA_2\gamma$ in agonist-stimulated AA release in intact cells. Accordingly, a chiral HPLC column was used to separate (R)-BEL and (S)-BEL from rac-BEL (FIG. 2). Separation of the BEL enantiomers under the conditions employed resulted in resolution of two major UV-absorbing peaks with an RT difference of approximately 2 mm. The first peak eluted at 18.8 mm (Peak A) while the second peak eluted at 20.5 mm (Peak B) (Relative retention time ($R_{RT}$) Peak A/Peak B=0.917) (FIG. 2). Integration of the areas of each peak were identical (within 1%), suggesting that the enantiomers of BEL had been separated. Proton NMR data demonstrated peaks with the anticipated chemical shifts and coupling constants as has previously been published (data not shown) (41). Moreover, electrospray ionization mass spectrometric analysis of the material in each peak revealed the presence of a lithiated doublet at 323.3 and 325.3 Daltons (consistent with the presence of a bromine atom) which was of equal intensity for each moiety. Re-injection of Peak A or Peak B onto the chiral column demonstrated that each purified moiety eluted at its previous retention time with negligible amounts of contaminating material demonstrating that, as expected, no equilibration had occurred. Finally, both peaks coeluted utilizing a non-chiral C18 HPLC column (data not shown).

Figure 3:
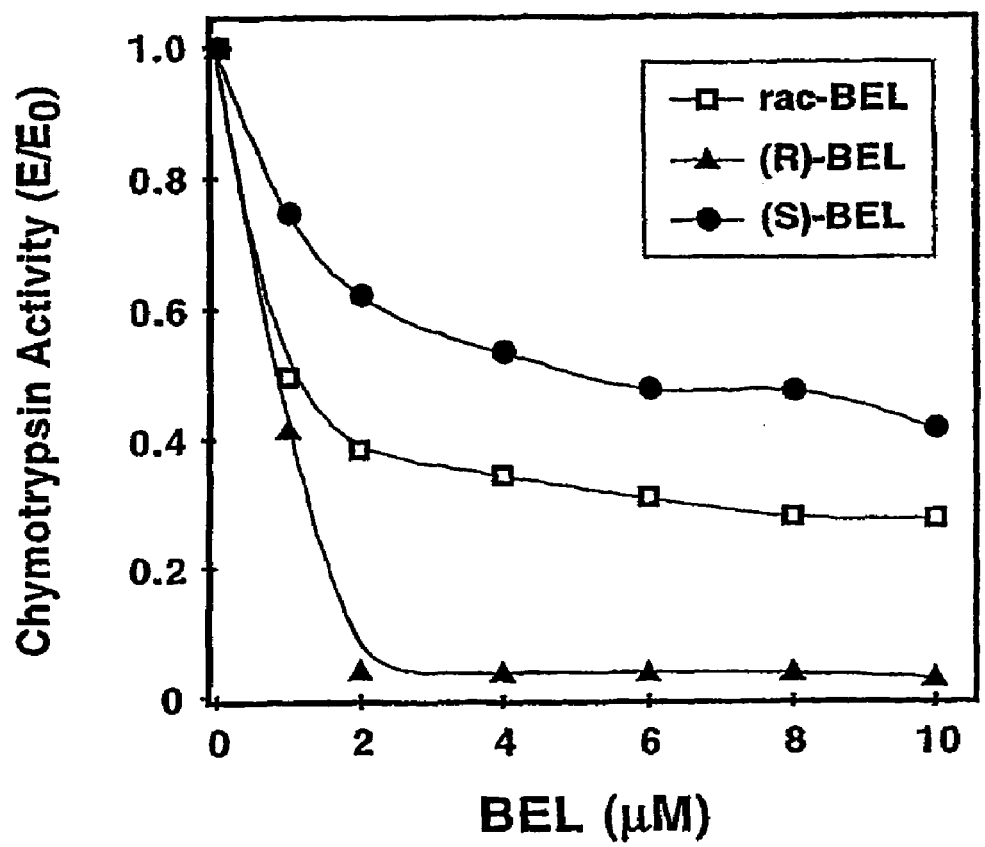
FIG. 3 depicts inhibition of α-chymotrypsin by racemic, (R)-and (S)-BEL.

Identification of the Absolute Chirality of the BEL Enantiomers—To determine the absolute chirality of the resolved BEL enantiomers, synthetic enantiomers of (F)-6-(iodomethylene)-3-(1-naphthalenyl)-2H-tetrahydropyran-2-one (αNpI6) of known chirality were chromatographed separately and together on the chiral stationary phase. Under these conditions, (S)-αNpI6 ($R_T$=19.5 min) eluted prior to (R)-αNpI6 ($R_T$=21.4 min) with approximately the same degree of separation ($R_{RT}$=0.911) as the BEL enantiomers. Chymotrypsin has previously been identified as a suitable target for aromatic haloenol lactones resulting in its mechanism-based inhibition as detailed by careful kinetic analyses by Katzenellenbogen (41-44). In prior studies, (R)-BEL was determined to be a more efficient inhibitor of chymotrypsin than (S)-BEL in comparison to its chiral counterpart (36). To further substantiate the absolute stereochemistry of the BEL enantiomers resolved by chiral HPLC and to confirm the ability of the resolved enantiomers to selectively inhibit chymotrypsin activity, increasing concentrations of (R)-BEL, (S)-BEL, or rac-BEL were incubated with chymotrypsin, and diluted in buffer as described in "Experimental Procedures". Activity assays were performed using the fluorogenic chymotrypsin substrate N-succinyl-Ala-Ala-Pro-Phe-7-amido-4-methyl-coumarin as described in "Experimental Procedures". Under the conditions employed, (R)-BEL stoichiometrically and irreversibly inhibited chymotrypsin while (S)-BEL was considerably less potent (FIG. 3). These results confirm that both peaks are distinct enantiomers of BEL and substantiate, by independent criteria, the assigned absolute stereochemistry of the peaks eluting from the chiral HPLC column.

Enantiomeric Selective inhibition of iPLA$_2\beta$ and iPLA$_2\gamma$—Previous experiments with iPLA$_2\beta$ and iPLA$_2\gamma$ have established that iPLA$_2\beta$ and iPLA$_2\gamma$ are inhibited by racemic BEL with an IC$_{50}$ range of 200 nM for iPLA$_2\beta$ and about 3 µM for iPLA$_2\gamma$ (24, 31). Accordingly, we next examined the ability of the resolved enantiomers of BEL to inhibit iPLA$_2\beta$ and iPLA$_2\gamma$. For these experiments, iPLA$_2\beta$ or iPLA$_2\gamma$ was pre-incubated with (R)-BEL, (S)-BEL, rac-BEL, or ethanol vehicle alone for 3 mm followed by measurement of remaining enzymatic activity utilizing a radiolabeled phospholipid substrate. Remarkably, (S)-BEL selectively inhibited iPLA$_2\beta$ 10-fold more potently than (R)-BEL (FIG. 4A). In stark contrast, (R)-BEL selectively inhibited iPLA$_2\gamma$ approximately 10-fold more potently than (5)-BEL (FIG. 4B). As anticipated, the inhibitory potency of racemic BEL was intermediate of that of (R)-BEL and (S)-BEL. Thus, (5)-BEL is a more potent inhibitor of iPLA$_2\beta$ while (R)-BEL is a more potent inhibitor of iPLA$_2\gamma$.

Figure 5:
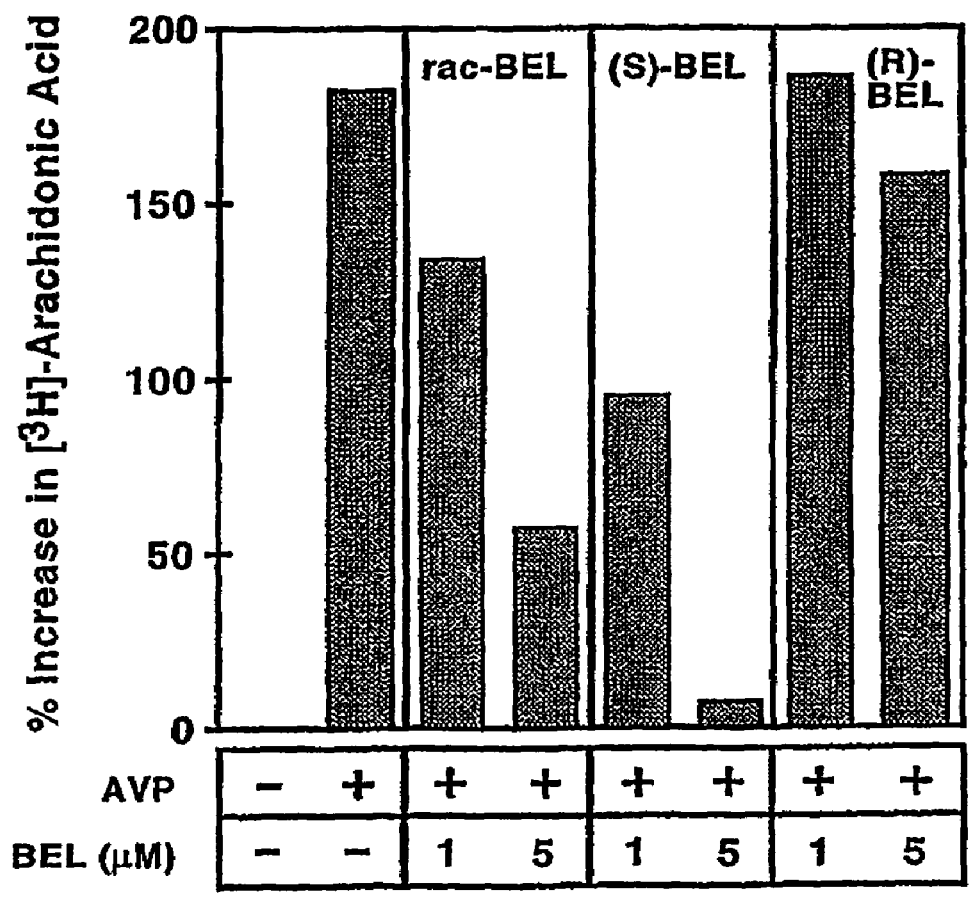
FIG. 5 depicts inhibition of AVP-mediated arachidonic acid liberation in A-10 smooth muscle cells.

Identification of iPLA2β and not iPLA2γ as the Mediator of AVP-induced AA Release in A-10 Cells—Upon stimulation with AVP, A-10 smooth muscle cells rapidly release a relatively large percentage (about 5%) of their esterified arachidonic acid (10). Prior studies have demonstrated that pretreatment of the cells with 2 to 5 µM BEL inhibits≈60 to 80%, respectively, of AVP-inducible arachidonic acid release (10, 29). Moreover, the absence of extracellular calcium ion (incubations performed in the presence of EGTA in the media) or the presence of intracellular calcium ion chelators (e.g. BAPTA) does not effect AVP-induced AA release in A-10 cells (29). Since combined incubations with EGTA and BAPTA completely ablated FURA-2 observable increases in intracellular calcium ions, these results further implicated the involvement of a calcium-independent phospholipase A$_2$ in this process. However, since both iPLA$_2\beta$ and the newly identified iPLA$_2\gamma$ are both inhibited by rac-BEL (and are calcium-independent), the identity of the iPLA$_2$ mediating AA release in AVP-stimulated A-10 cells was unknown. To address this issue, we exploited the selectivity of (S)-BEL and (R)-BEL, for inhibition of iPLA$_2\beta$ and iPLA$_2\gamma$, respectively, to determine the type of iPLA$_2$ catalyzing AVP-induced release of [$^3$H]-armchidonic acid from A-10 cells. As previously demonstrated, A-10 cells stimulated with AVP results in a substantial increase in the amount of nonesterified [$^3$H]-arachidonic acid relative to control cells incubated with vehicle alone (FIG. 5). This AVP-induced increase in non-esterified [$^3$H]-arachidonic acid is significantly reduced in the presence of low concentrations of rac-BEL (1 and 5 µM) (FIG. 5). Importantly, (S)-BEL (1 µM) substantially inhibited AA release (50% inhibition) and 5 µM (S)-BEL completely attenuated AVP-induced AA release. In sharp contrast, (R)-BEL is virtually ineffective (about 10% inhibition at 5 µM BEL) in inhibiting AVP-induced AA release from A-10 cells under similar conditions (FIG. 5). Thus, iPLA$_2\beta$, and not iPLA$_2\gamma$, is the likely mediator of AA release in this system.

Figure 7:
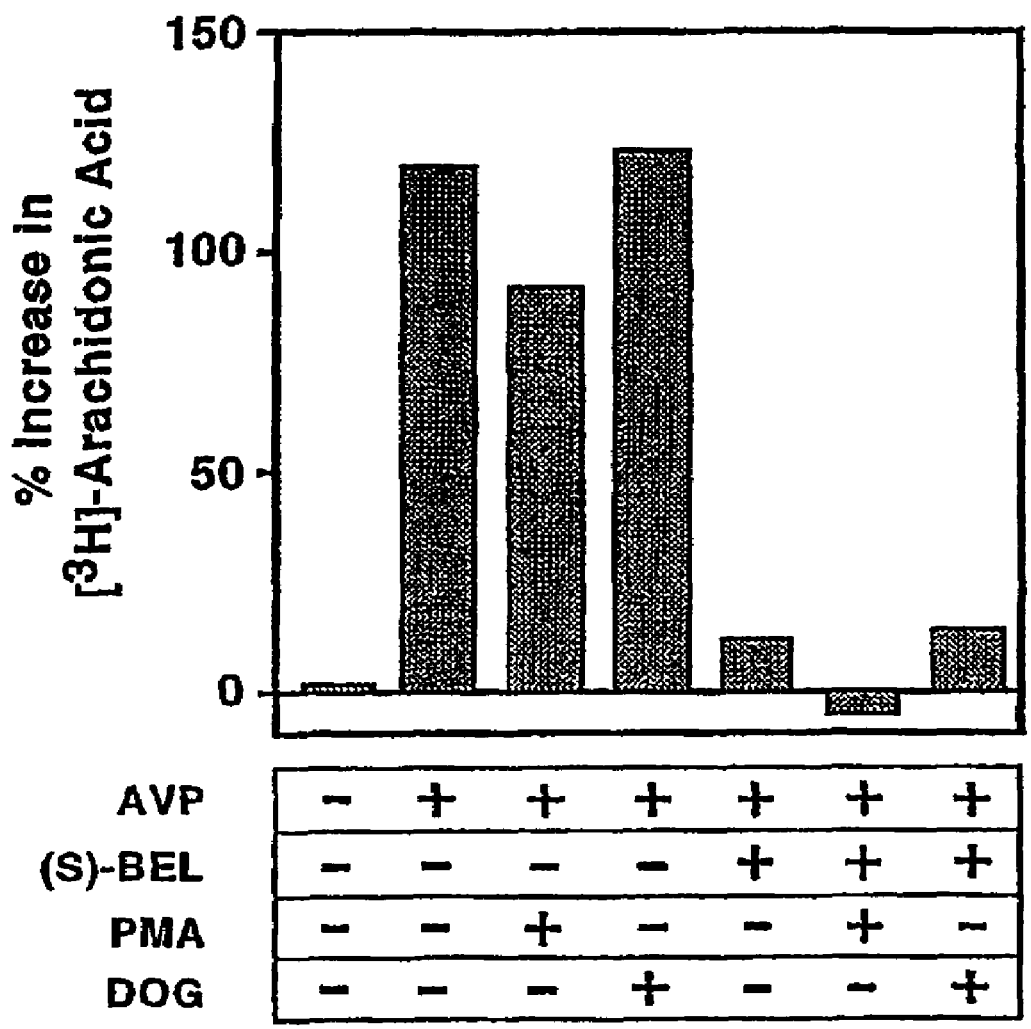
FIG. 7 depicts inability of phorbol-12-myristate-13-acetate and 1,2-dioctanoyl-sn-glycerol to reconstitute arachidonic acid liberation in A-10 cells treated with (S)-BEL.
Figure 8:
FIG. 8 depicts translocation of PKCδ and PKCε in A-10 smooth muscle cells is unaffected by pre-treatment with (S)-BEL
Figure 8:
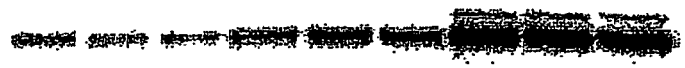
Figure 8:
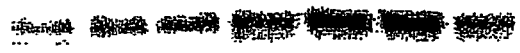
Figure 8:
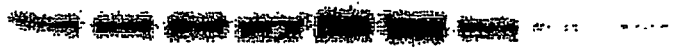
Figure 8:
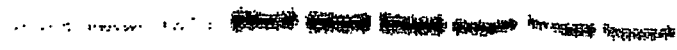
Figure 9:
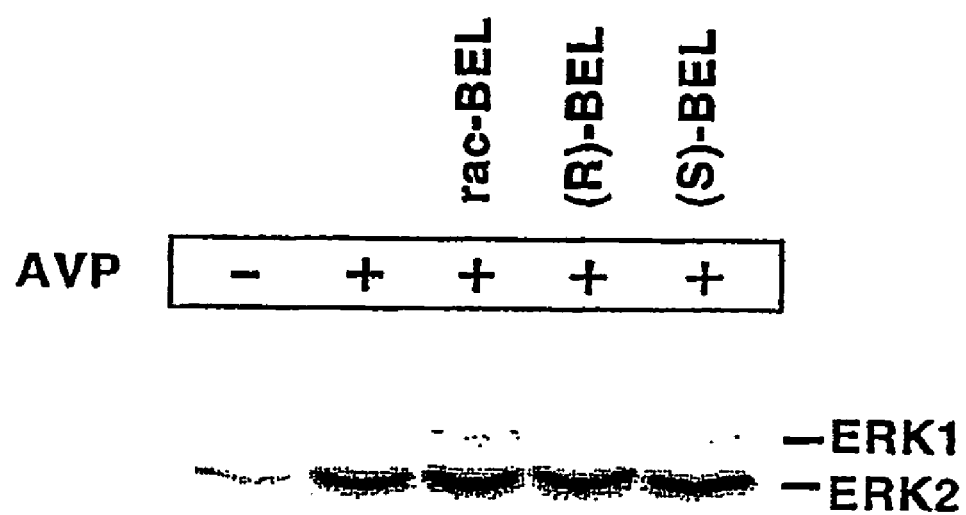
FIG. 9 depicts racemic BEL, (R)-BEL, or (S)-BEL do not inhibit AVP-induced MAPK phosphorylation.

Confirmation of the Lack of Effects of BEL on Processes Typically Associated with cPLA2α Activation—Activation of cPLA2α in most systems depends on the concomitant activation of MAPK, PKC, and increases in intracellular [Ca$^{2+}$] (45-47). In prior studies we demonstrated that BEL does not inhibit AVP-induced increases in [Ca$^{2+}$]$_1$, and that ablation of changes in [Ca$^{2+}$] by BAPTA does not attenuate AA release (29). Recently, Dennis and coworkers have suggested that cytosolic phosphatidate phosphohydrolase (PAP-1) in some cell types may be a target for BEL and that the resulting inhibition of PAP-1 would result in diminished levels of diacylglycerol produced from phosphatidic acid, thereby attenuating PKC activation precluding cPLA$_2\alpha$ activation and AA release (33, 34). To address this possibility, we first examined the effects of rac-BEL on A-10 cell PAP activities in cytosol and membrane fractions (FIG. 6A) as well as in intact cells (FIG. 6B). These tests consistently demonstrated the lack of any effect of BEL on either the cytosolic (PAP-1) or the membrane-bound (PAP-2) forms of A-10 cell phosphatidate phosphohydrolase at concentrations up to 200 µM BEL (FIG. 6A). Furthermore, homogenates from intact A-10 cells previously exposed to up to 100 µM racemic BEL did not inhibit total phosphatidate phosphohydrolase activity in comparison to ethanol-treated controls (FIG. 6B). Next, we examined whether activation of PKC by exogenous addition of either phorbol-12-myristate-13-acetate (PMA) or 1,2-dioctanoyl-sn-glycerol (DOG) could rescue AA release after BEL pretreatment. Neither PMA or DOG could restore the ability of (S)-BEL treated A-10 cells to release arachidonic acid, thereby demonstrating that BEL is likely inhibiting arachidonic acid release in a manner which is no longer responsive to PKC activation (i.e. irreversible covalent modification of iPLA$_2$) (FIG. 7). A-10 cells contain at least four PKC isoforms, PKC$_\alpha$, PKC$_\delta$, PKC$_\epsilon$, and PKC$_{12}$, by Western blot analysis (FIG. 8), however no bands corresponding to PKC$_{\beta I}$, PKC$_{\beta II}$, PKC$_\gamma$, PKC$_\eta$, or PKC$_\zeta$ could be visualized previously. Accordingly, we treated A-10 cells with AVP and determined if (S)-BEL could inhibit PKC translocation to the membrane fraction. Stimulation of A-10 cells with AVP causes translocation of PKC$_\delta$ and PKC$_\epsilon$ from the cytosol to the membrane fraction, but neither PKC$_\alpha$ nor PKC$_\iota$ undergo AVP-induced translocation in A-10 cells (FIG. 8). Pretreatment of A-10 cells with 5 µM (S)-BEL, which causes almost complete inhibition of AA release, does not effect the translocation of either PKC$_\delta$ or PKC$_\epsilon$ (FIG. 8). Finally, AVP-induced phosphorylation of ERK2 is not effected by the presence of 5 µM (R)-, (5)-, or rac-BEL (FIG. 9). Collectively, these results demonstrate that 1) neither PAP-1 nor PAP-2 is a target for BEL in A-10 smooth muscle cells; 2) BEL does not appreciably effect PKC$_\delta$ and PKC$_\epsilon$ translocation or MAPK phosphorylation in A-10 cells; and 3) iPLA$_2\beta$ is likely responsible for the large majority of arachidonic acid release from A-10 cells.

Discussion—Genetic approaches have now demonstrated the presence of two types of iPLA$_2$ activities present in the human genome (iPLA$_2\beta$ and iPLA$_2\gamma$) which are both inhibited by rac-BEL (24, 31, 32). Accordingly, all prior tests demonstrating inhibition of arachidonic acid release by rac-BEL cannot discriminate between hydrolysis catalyzed by iPLA$_2\beta$ or that mediated by iPLA$_2\alpha$. Virtually nothing is known about the regulation of iPLA$_2\gamma$ or its potential role in agonist-stimulated eicosanoid release. In this work, we: 1) resolve rac-BEL by chiral HPLC; 2) assign the absolute stereochemistry of the resolved enantiomers by two independent techniques; 3) demonstrate a 10-fold selectivity of (S)-BEL for inhibition of iPLA$_2\beta$ and a 10-fold selectivity of (R)-BEL for inhibition of iPLA2γ; 4) demonstrate that (S)-BEL inhibits that vast majority of AVP-induced AA liberation in A-10 cells while (R)-BEL does not; 5) provide evidence that BEL-mediated inhibition of AA release in A-10 cells is not mediated through inhibition of either membrane-bound or cytosolic phosphatidate phosphohydrolases; and 6) demonstrate that treatment of A-10 cells with (S)-BEL does not attenuate PKC translocation or MAPK activation after AVP stimulation. Collectively, these results, in combination with work (see below) demonstrates that AVP-stimulated AA release in A-10 cells is likely mediated by iPLA$_2\beta$ and not iPLA2γ, cPLA$_2\alpha$, or chymotrypsin-like proteases.

The utilization of chiral pharmacologic agents instead of racemic mixtures has increasingly been appreciated to enhance the potency of inhibitors toward targeted processes and markedly reduce toxicity and "non-specific inhibition" mediated by interactions with non-targeted systems. Since enzymes possess multiple chiral centers, the interaction between a chiral inhibitor and one or more optically active centers at or near the enzyme active site results in diastereotopic interactions which possess different physical properties and spatial relationships for each diastereotopic pair. In the case of mechanism-based inhibitors such as BEL, these diastereotopic interactions are anticipated to: 1) alter binding; 2) modify the rate of formation of the acyl-enzyme intermediate; and 3) alter the covalent trapping of the halomethyl ketone in the acyl enzyme by nucleophiles at or near the active site. In this study, we have exploited diastereotopic interactions between individual enantiomers of BEL and the known mammalian iPLA$_2$s (i.e. iPLA$_2\beta$ and iPLA$_2\gamma$) to achieve a remarkable specificity for inhibition of iPLA$_2\beta$ by (S)-BEL and iPLA$_2\gamma$ by (R)-BEL, respectively. Moreover, we demonstrated that proteases with similar stereochemical relationships as chymotrypsin are more likely to be inhibited by (R)-BEL than (S)-BEL, thereby further increasing the utility of mechanism-based inhibition to gain insight into the types of phospholipases A2 mediating AA release in mammalian cells.

With any pharmacologic compound, unanticipated effects on non-targeted systems may occur with increasing likelihood at high concentrations of inhibitor. Mammalian cells have in excess of 30,000 genes which after splicing and post-translational modification give rise to well over $10^5$ and perhaps as many as $10^6$ different chemical moieties. Of course, it is impossible to test every compound with each of these chemical moieties in each different microenvironment in the cell in which pharmacologic agents might interact. Indeed, at high enough concentrations in aqueous systems, virtually any low molecular weight organic compound will interact with a diverse array of proteins due to hydrophobic effects alone. That is precisely why it is important to examine biologic effects elicited by pharmacologic agents at or near their effective inhibitory concentrations in intact cells as was determined in isolated purified systems. In the case of BEL, some investigators have employed 50-100 μM BEL which exceeds the effective inhibitory concentration of BEL for the known mammalian iPLA$_2$s by two orders of magnitude. Accordingly, these tests must be interpreted with caution given the IC$_{50}$ of rac-BEL for iPLA$_2\beta$ and iPLA$_2\gamma$ is in the 0.5-3 μM range. Moreover, the mere exposure of cells to high concentrations of organic compounds (50-100 μM) is likely to perturb the fragile order of the membrane microenvironment and, in the case of investigating membrane-related phenomena, may have effects which are independent of interactions with targeted enzyme systems alone. Indeed, we have observed cell death employing 100 μM BEL which is almost certainly independent of the effects of BEL on targeted processes.

Dennis and co-workers have contended that high concentrations of rac-BEL (≈25 μM) effectively inhibit magnesium-dependent cytosolic phosphatidate phosphohydrolase (PAP-1) in mouse P388D1 macrophages (33) and human amnionic WISH cells (34). The authors argue that inhibition of PAP-1 would be expected to cause a deficiency in DAG thus blunting PKC activation and possibly activation of cPLA2a by MAPK. However, BEL has been subsequently shown not to affect PMA-induced translocation of PKC (or PKC catalytic activity) in P388D1 macrophages (15) or MAPK phosphorylation in WISH cells (34), rat neutrophils (48), and A-10 cells (this application). It should be mentioned that in their investigations, Balsinde et al. did not observe any effect of BEL on PAP-2 (33), the phosphatidate phosphohydrolase isoform which is believed to be involved in lipid signal transduction pathways (49-51). This absence of PAP-2 inhibition by BEL has since been observed in McA-RH7777 rat hepatoma cells (17), pancreatic islet cells (52), and A-10 smooth muscle cells (this application). Furthermore, cytosolic PAP-1 activity in McA-RH7777 cells is not significantly inhibited by 100 μM BEL (17). A second possible effect of inhibited PAP-catalyzed DAG production, as described by Balboa et al. (34), is that the phospholipid substrate will be in a sub-optimal environment since DAG has been demonstrated to alter membrane bilayers by creating more distance between phospholipid headgroups, thereby making the phospholipid ester linkages more susceptible to PLA$_2$-mediated hydrolysis. However, we have found that rac-BEL does not inhibit release of IP$_2$ or IP$_3$ in A-10 cells (10) and Akiba et al. (15) have found that BEL (up to 5 μM) does not significantly effect levels of diacylglycerol or phosphatidic acid formed in P388D1 macrophages upon stimulation with zymosan.

The identification of chiral specificity of individual enantiomers of BEL to inhibit the known mammalian iPLA$_2$s extends the utility of mechanism-based inhibitors in the study of agonist-mediated AA release. The tests described herein allow assignment of AVP-induced AA release in A-10 cells to iPLA$_2\beta$ and not iPLA$_2\gamma$. The inhibition of AA release by (S)-BEL and not (R)-BEL excludes participation of chymotrypsin or chymotrypsin-like proteases in these processes. Finally, the utilization of chiral mechanism-based inhibitors reduces potential "non-specific" complications through comparisons of the effects of specific optical antipodes on the observed end points (i.e. AA release) with their in vitro potency in purified systems. Assignation of specific enzymes as effectors of AA release requires detailed concurrent consideration of biochemical, pharmacologic, and genetic perturbations on the observed process. In the case of AVP-induced AA release from A-10 cells, we have: 1) demonstrated that concentrations of (S)-BEL near the IC$_{50}$ for iPLA$_2\beta$ dramatically attenuate AA release in intact A-10 cells while (R)-BEL does not (this application); 2) demonstrated that BEL-mediated inhibition of AA release occurs in the presence of normal increases in [Ca$^{2+}$]1 (29) and cannot be rescued by exogenous activation of PKC by PIVIA or DOG (this application); 3) that AVP-mediated AA release in A-10 cells is not affected by removal of calcium ions from the external media or by effective buffering internal calcium concentration by BAPTA-AM (entry of extracellular calcium and increases in [Ca$^{2+}$]1 are each thought to be necessary for cPLA$_2\alpha$ activation (53-55)); and 4) that many other enzymes thought to be necessary or associated with AA release are not inhibited by the concentrations of BEL employed. For example, enzymes which participate in signal transduction cascades which are known not to be inhibited by the concentrations of BEL employed include: phosphatidylinositol-specific phospholipase C (10), phospholipase D (17), protein kinase A (56), and channels which mediate Ca$^{2+}$ release from intracellular stores (10). Of course, as with any other process, we can not rule out the involvement of as yet undiscovered phospholipases or activation cascades. However, we state that in the presence of PKC activation, MAPK activation, and increases in [Ca$^{2+}$], (processes typically deemed necessary for cPLA2a-mediated AA release), arachidonic acid release is still inhibited by (S)-BEL with a dose response profile and chiral selectivity which closely corresponds to iPLA$_2\beta$.

DETAILED DESCRIPTION OF THE DRAWINGS

FIG. 1—shows the calcium-independent phospholipase A$_2$ (iPLA$_2$) gene family and sequence alignment of iPLA$_2$ nucleotide and lipase consensus motifs. Members of the iPLA$_2$ gene family ($\alpha$, $\beta$, and $\gamma$) are aligned according to their nucleotide-binding motifs (boxed diagonal bars) and, lipase consensus sites (filled bars). Calcium-independent phospholipase A$_2\beta$ contains eight ankyrin repeat domains (gray bars) and a calmodulin-binding domain (CaM) near the C-terminus (boxed horizontal bars).

FIG. 2 shows separation of BEL enantiomers by chiral HPLC. A Chirex 3,5-dinitrobenzoyl-(R)-phenylglycine chiral HPLC column (4.6 mm×25 cm) was equilibrated with hexane/dichloroethane/ethanol (150/115/1) at a flow rate of 2 ml/min. Racemic BEL (10 nmol) was injected onto the column as feed and the UV absorbance (280 nm) was recorded for the time indicated. The elution time for the (S) enantiomer (Peak A) was 18.8 mm and that for the (R) enantiomer (Peak B) was 20.5 mm. The chemical structures of (R)- and (S)-BEL are as indicated above the chromatogram.

FIG. 3 shows inhibition of $\alpha$-chymotrypsin by racemic, (R)-, and (S)-BEL. Chymotrypsin (2 µM) in 0.1 M sodium phosphate buffer, pH 7.2 was incubated with the indicated concentrations of racemic, (R)-, or (S)-BEL for 5 mm. This solution was then diluted 1000-fold in 0.1 M sodium phosphate buffer, pH 7.2 containing 100 mM hydrazine and incubated for 1 hr at 22° C. Chymotrypsin proteolytic activity was measured spectrofluorometrically using N-succinyl-Ala-Ala-Pro-Phe-7-amido-4-methylcoumarin (50 µM) as substrate.

Figure 4:
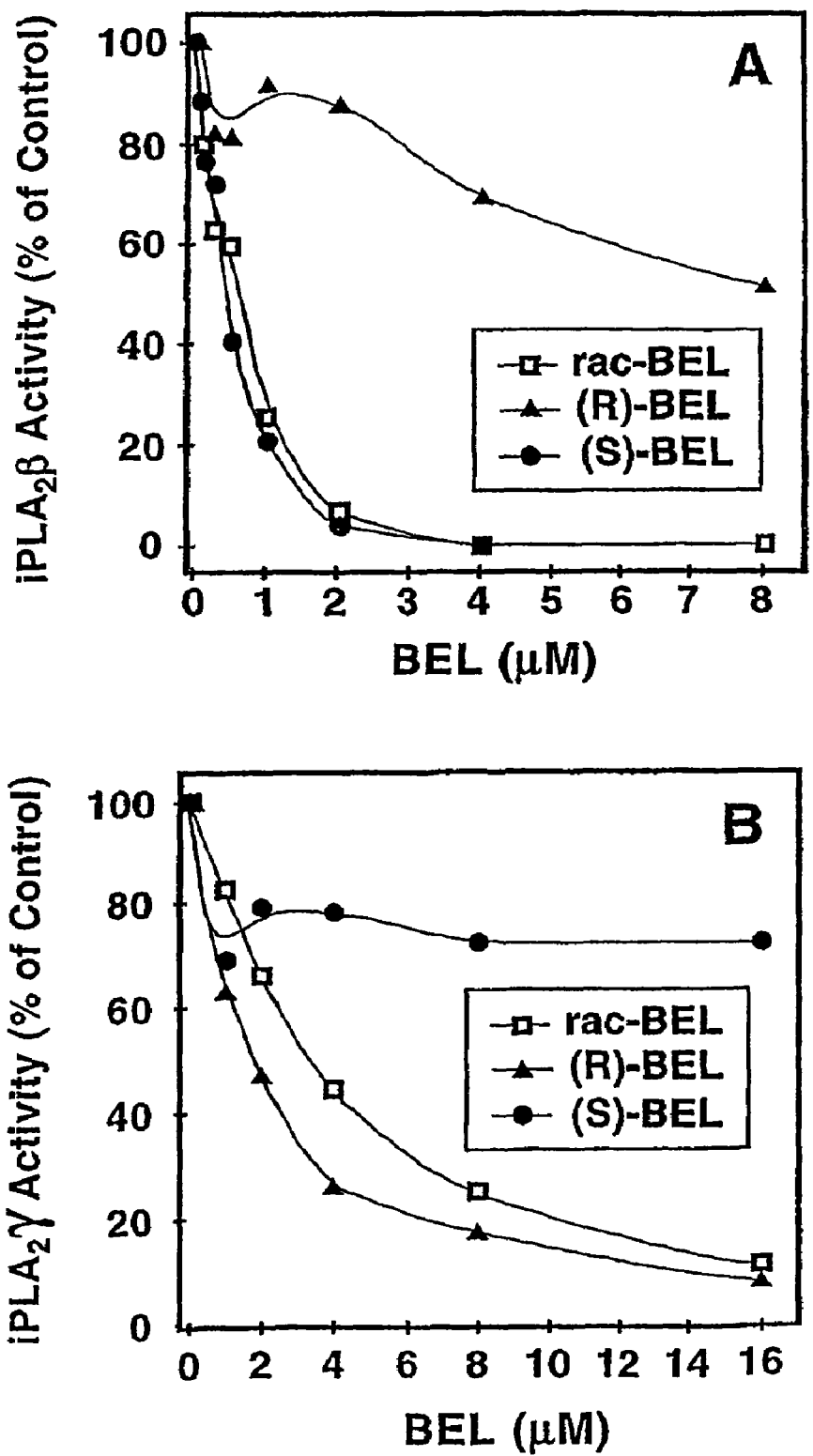
FIG. 4 depicts selective inhibition of iPLA$_2$β and iPLA$_2$γ by racemic, (R)-, and (S)-BEL.

FIG. 4 shows selective inhibition of iPLA$_2\beta$ and iPLA$_2\gamma$ by racemic, (R)-, and (S)-BEL. Panel A—Purified recombinant iPLA$_2\beta$ (1 µg/ml) in 100 mM Tris-HCl, pH 7.3 containing 1 mM EGTA was preincubated at 22° C. for 3 mm in the presence of the indicated concentrations of (R)-, (S)-, or rac-BEL or ethanol vehicle alone (1% final concentration). Radiolabeled substrate (L-$\alpha$-1-palmitoyl-2-[1-$^{14}$C]-arachidonyl-phosphatidylcholine, 5 µM final concentration) was then added to each reaction and incubated at 37° C. for 2 min. Reactions were terminated by extraction of remaining substrate and products into butanol, separation by TLC, and quantification of released radiolabeled fatty acid by scintillation spectrometry as described in Experimental Procedures. Results are representative of four separate tests. Panel B—Washed Sf9 cell membranes containing recombinant human iPLA$_2\gamma$ were preincubated for 3 min with the indicated concentrations of (R)-, (S)-, or racemic BEL or ethanol vehicle alone (1% final concentration) in 100 mM Tris-acetate, pH 8.0 containing 1 mM EGTA at 22° C. Radiolabeled substrate (L-$\alpha$-1-palmitoyl-2-[1-$^{14}$C]-oleoyl-phosphatidylcholine, 5 µM final concentration) was then added to each reaction and incubated at 37° C. for 2 min. Reactions were terminated by extraction of remaining substrate and products into butanol, separation by TLC, and quantification of released radiolabeled fatty acid by scintillation spectrometry as described in "Experimental Procedures". Results are representative of four separate tests.

FIG. 5 shows inhibition of AVP-mediated arachidonic acid liberation in A-10 smooth muscle cells by racemic, (R)-, and (S)-BEL. A-10 cells (2.5×10$^5$ cells/dish) were radiolabeled with [$^3$H]-arachidonic acid (0.5 µCi/dish) for 20 hrs. After washing to remove unincorporated [$^3$H]-arachidonic acid, cells were then incubated with either 1 µM or 5 µM (R)-BEL, (S)-BEL, rac-BEL, or ethanol vehicle (0.1%) in DMEM for 20 mm. This media was removed and the cells were then incubated with 3 ml of DMEM containing 10% heat-inactivated fetal bovine serum with or without 1 µM AVP. After 5 min, 1 ml of this medium was removed and lipids were extracted into 2 ml of chloroform/methanol/acetic acid (25:24:1). The remaining cells were scraped into 1 ml of deionized water and total lipids were extracted as described above. The chloroform layer was evaporated under nitrogen and the extracted lipids were separated by TLC. Regions containing fatty acids and phospholipids were scraped into vials and radioactivity was quantified by liquid scintillation spectrometry. Results are representative of four separate tests.

Figure 6:
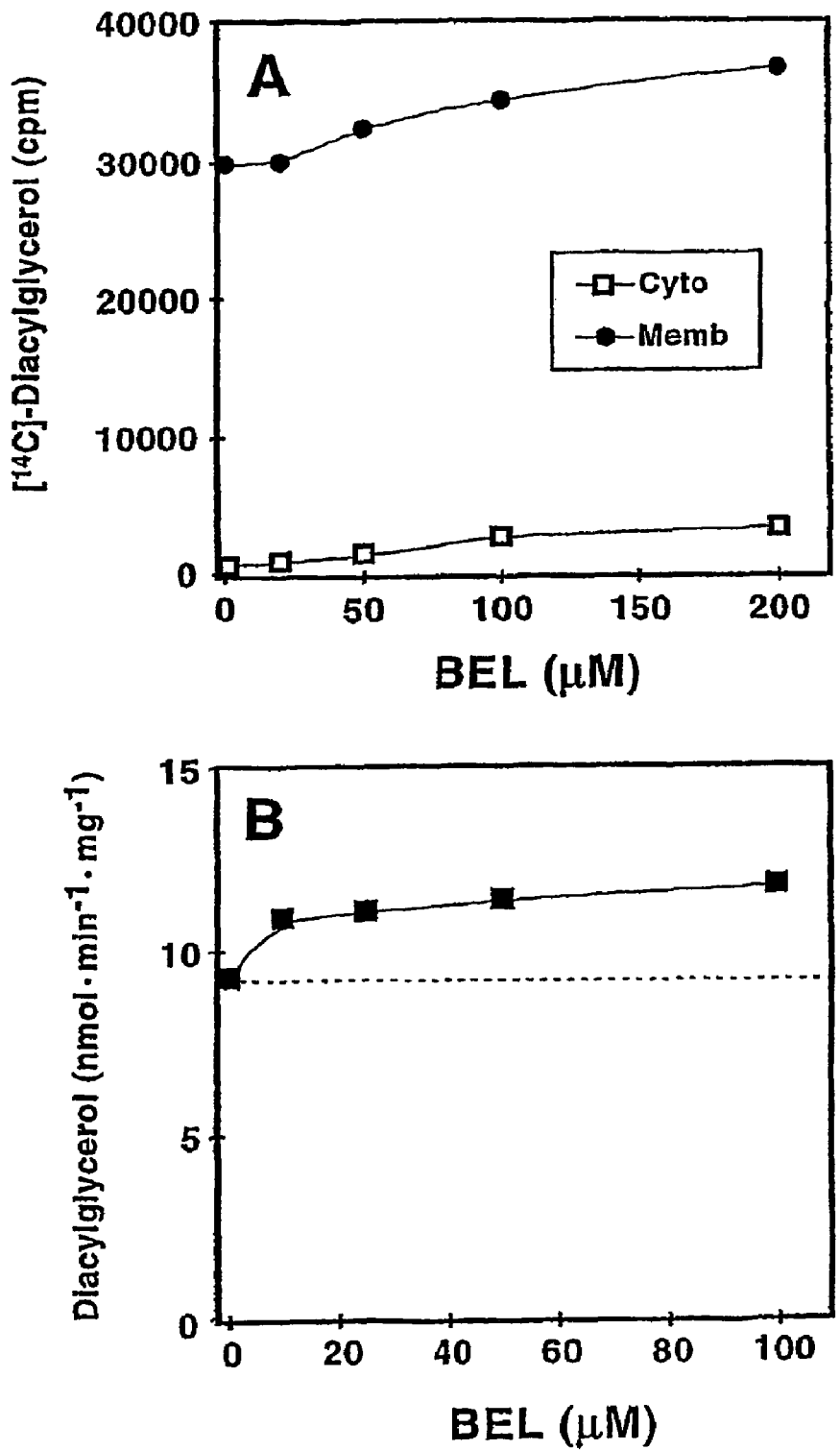
FIG. 6 depicts inability of racemic BEL to inhibit A-10 smooth muscle cell cytosolic (PAP-1) and membrane-bound (PAP-2) phosphatidate phosphohydrolase activities.

FIG. 6 shows the inability of racemic BEL to inhibit A-10 smooth muscle cell cytosolic (PAP-1) and membrane-bound (PAP-2) phosphatidate phosphohydrolase activities. A-10 cells plated on 100 mm dishes were washed 2× in ice-cold PBS and harvested in lysis buffer (50 mM Tris-HCl, pH 7.4 containing 0.25 M sucrose and 0.2 mM DTT). After briefly sonicating, cytosolic and membrane fractions were separated by ultracentrifugation before measuring phosphatidate phosphohydrolase activity. In panel A, cytosolic or membrane fractions were pre-incubated with rac-BEL (up to 200 µM) or ethanol vehicle at 22° C. for 5 min in the presence of 50 mM Tris-HCl, pH 7.2 containing 10 mM $\beta$-mercaptoethanol, 2 mM MgCl$_2$, and 1 mM EGTA. Dipalmitoyl phosphatidic acid (100 µM final concentration containing 0.05 µCi L-$\alpha$-dipalmitoyl [glycerol-$^{14}$C(U)]-phosphatidic acid per reaction in the presence of 1 mM Triton X-100) was added to each reaction which was then transferred to a 37° C. water bath for 5 (membrane fraction) or 10 (cytosolic fraction) mm. Reaction products were terminated with the addition of 5% acetic acid, extracted into chloroform, dried under nitrogen, and resolved by TLC as described in "Experimental Procedures". Results are representative of three separate tests. In panel B, intact A-10 cells were washed and pretreated with BEL or ethanol vehicle (as described in FIG. 5) before isolation of the cell homogenate and quantification of phosphatidate phosphohydrolase activity as described above. Results are representative of three separate tests.

FIG. 7 shows the inability of phorbol-12-myristate-13-acetate and 1,2-dioctanoyl-sn-glycerol to reconstitute arachidonic acid liberation in A-10 cells treated with (S)-BEL. A-10 cells were radiolabeled with [$^3$H]-arachidonic acid, washed, and pre-incubated with 5 µM (S)-BEL or ethanol vehicle alone for 15 min as described in FIG. 5. DMEM media containing 10% heat-inactivated fetal bovine serum with or without 1 µM AVP was then added to the cells. PMA (1 µM) or DOG (10 µM) were included in this media as indicated in the figure. After 5 min at 37° C., [$^3$H]-arachidonic acid released into the media and remaining within the cells (free and incorporated into phospholipids) was extracted into chloroform, separated by TLC, and quantified by liquid scintillation spectrometry as described in "Experimental Procedures". Results are representative of three separate tests.

FIG. 8 shows that translocation of PKC$\delta$ and PKC$\epsilon$ in A-10 smooth muscle cells is unaffected by pre-treatment with (S)-BEL. A-10 cells were incubated in the presence of 5 µM (S)-BEL or ethanol vehicle in DMEM without serum for 15 min at 37° C., followed by removal of the medium, and incubation in the presence or absence of 1 µM AVP in DMEM for 5 min as indicated in the figure. After lysis of the cells, low speed pellets (LSP) obtained by centrifugation at 1,000×g, membrane (Memb), and cytosolic (Cyto) fractions (obtained by centrifugation at 100,000×g) were electrophoresed by SDS-PAGE (20 µg of protein per lane) and immunoreactive bands corresponding to the indicated PKC isoforms ($\alpha$, $\delta$, $\epsilon$, and ι) were visualized by ECL Western analysis as described in "Experimental Procedures".

FIG. 9 shows that racemic BEL, (R)-BEL, or (S)-BEL do not inhibit AVP-induced MAPK phosphorylation. A-10 cells were incubated in the presence of ethanol vehicle or 5 µM rac-BEL, (R)-BEL, or (S)-BEL in DMEM for 15 min at 37° C. After removal of this media, the cells were incubated for 5 min in the presence or absence of 1 µM AVP as indicated in the figure, washed with ice-cold PBS, and then lysed with RIPA buffer. Extracts from the cells were separated by SDS-PAGE (20 µg protein per lane), transferred to a PVDF membrane, and analyzed by ECL immunoblotting for phosphorylated MAPK as described in "Experimental Procedures".

ABBREVIATIONS

AVP—Arginine vasopressin
BEL is (E)-6-(bromomethylene)-3-(1-naphthalenyl)-2H-tetrahydropyran-2-one
Rac-BEL—Racemic (E)-6-(bromomethylene)-3-(1-naphthalenyl)-2H-tetrahydropyran-2-one
(R)-BEL—(R)(E)-6-(bromomethylene)-3-(1-naphthalenyl)-2H-tetrahydropyran-2-one
(S)-BEL—(S)(E)-6-(bromomethylene)-3-(1-naphthalenyl)-2H-tetrahydropyran-2-one
αNpI6—(E)-6-(iodomethylene)-3-(1-naphthalenyl)-2H-tetrahydropyran-2-one
EGTA—Ethylene glycol-bis(β-aminoethyl ether)-N,N,N',N'-tetraacetic acid
$cPLA_2$—Cytosolic phospholipase $A_2$
$iPLA_2$—Calcium-independent phospholipase $A_2$
$iPLA_2\beta$—Calcium-independent phospholipase $A_2\beta$
$iPLA_2\gamma$—Calcium-independent phospholipase $A_2\gamma$
PAP—Phosphatidate phosphohydrolase
PMA—Phorbol-12-myristate-13-acetate
DOG—1,2-Dioctanoyl-sn-glycerol
$R_{RT}$—Relative retention time
Rac-BEL=racemic BEL

REFERENCES

1. Gross, R. W. (1998) Biochem. Soc. Trans. 26, 345-349
2. Farooqui, A. A., Yang, H-C., Rosenberger, T. A., and Horrocks, L. A. (1997) J. Neurochem. 69, 889-901
3. Ma, Z. and Turk, J. (2001) Prog. Nucleic Acid Res. Mol. Biol. 67, 1-33
4. Miyake, R. and Gross, R. W. (1992) Biochim. Biophys. Acta 1165, 167-176
5. Gross, R. W., Ramanadham, S., Kruszka, K K., Han, X., and Turk, J. (1993) Biochemistry 32, 327-336
6. Ramanadham, S., Wolf, M. J., Jett, P. A., Gross, R. W., and Turk, J. (1994) Biochemistry 33, 7442-7452
7. Wolf, R. A. and Gross, R. W. (1985) J. Biol. Chem. 260, 7295-7303
8. McHowat, J. and Creer, M. H. (1998) Lipids 33, 1203-1212
9. Wolf, M. J., Izumi, Y, Zorumski, C. F., and Gross, R. W. (1995) FEBS Lett. 377, 358-362
10. Lehman, J. J., Brown, K. A., Ramanadham, S., Turk, J., and Gross, R. W. (1993) J. Biol. Chem. 268, 20713-20716
11. Gross, R. W., Rudolph, A. E., Wang, J., Sommers, C. D., and Wolf, M. J. (1995) J. Biol. Chem. 270, 14855-14858
12. McHowat, J., Liu, S., and Creer, M. H. (1998) Ann. J. Physiol. 274, C1727-C1737
13. Atsumi, G, Tajima, M., Hadano, A., Nakatani, Y, Murakami, M., and Kudo, I. (1998) J. Biol. Chem. 273, 13870-13877
14. Murakami, M., Kambe, T., Shimbara, S., Kudo, I. (1999) J. Biol. Chem. 274, 3103-3115
15. Akiba, S., Mizunaga, S., Kume, K., Hayama, M., Sato, T. (1999) J. Biol. Chem. 274, 19906-19912
16. Roshak, A. K, Capper, E. A., Stevenson, C., Eichman, C., and Marshall, L. A. (2000) J. Biol. Chem. 275, 35692-35698
17. Tran, K, Wang, Y, DeLong, C. J., Cui, Z., and Yao, Z. (2000) J. Biol. Chem. 275, 25023-25030
18. Alzola, E., Peréz-Etxebarria, A., Kabré, E., Fogarty, D. J., Métioui, M., Chaïb, N., Macarulla, J. M., Matute, C., Dehaye, J-P., and Marino, A. (1998) J. Biol. Chem. 273, 30208-30217
19. Atsumi, G, Murakami, M., Kojima, K, Hadano, A., Tajima, M., and Kudo, I. (2000) J. Biol. Chem. 275, 18248-18258
20. McHowat, J., Kell, P. J., O'Neill, H. B., and Creer, M. H. (2001) Biochemistry 40, 14921-14931
21. Isenovic, E. and LaPointe, M. C. (2000) Hypertension 35, 249-254
22 Andrews, D. L., Beames, B., Summers, M. D., and Park, W. D. (1988) Biochem. J. 252, 199-206
23. Tang, J., Kriz, R. W., Wolfman, N., Shaffer, M., Seehra, J. and Jones, S. S. (1997) J. Biol. Chem. 272, 8567-8575
24. Mancuso, D. J., Jenkins, C. M., and Gross, R. W. (2000) J. Biol. Chem. 275, 9937-9945
25. Ma, Z., Ramanadham, S., Kempe, K., Sheny Chi, X., Landenson, J., and Turk, J. (1997) J. Biol. Chem. 272, 11118-11127
26. Jenkins, C. M., Wolf, M. J., Mancuso, D. J., and Gross, R. W. (2001) J. Biol. Chem. 276, 7129-7135
27. Wolf, M. J. and Gross, R. W. (1996) J. Biol. Chem. 271, 20989-20992
28. Wolf, M. J., Wang, J., Turk, J., and Gross, R. W. (1997) J. Biol. Chem. 272, 1522-1526
29. Nowatzke, W., Ramanadham, S., Ma, Z, Hsu, F-F., Bohrer, A., and Turk, J. (1998) Endocrinology 139, 4073-4085
30. Hazen, S. L., Zupan, L. A., Weiss, R. H., Getman, D. P., and Gross, R. W. (1991) J. Biol. Chem. 266, 7227-7232
31. Zupan, L. A., Weiss, R. H., Hazen, S. L., Parnas, B. L., Aston, K. W., Lennon, P. J., Getman, D. P., and Gross, R. W. (1993) J. Med. Chem. 36, 95-100
32. Balsinde, J. and Dennis, E. A. (1996) J. Biol. Chem. 271, 31937-31941
33. Balboa, M. A., Balsinde, J., and Dennis, E. A. (1998) J. Biol. Chem. 273, 7684-7690
34. Wolf, M. J. and Gross, R. W. (1996) J. Biol. Chem. 271, 30879-30885
35. Baek D-J. and Katzenellenbogen, J. A. (1991) Biochem. Biophys. Res. Comm. 178, 1335-1342
36. Dixon and Neurath (1957) J. Biol. Chem. 225, 10491059
37. Bligh, E. C and Dyer, W. J. (19) Can. J. Biochem. Physiol. 31, 911-917
38. Laemmli, U. K. (1970) Nature 227, 680-685
39. Ikegaki, N. and Kennett, R. H. (1989) J. Immunol. Meth. 124, 205-210
40. Daniels, S. B., Cooney, E., Sofia, M. J., Chakravarty, P. K., and Katzenellenbogen, J. A. (1983) J. Biol. Chem. 258, 15046-15053
41. _____
42. Chakravarty, P. K., Krafft, G. A., and Katzenellenbogen, J. A. (1982) J. Biol. Chem. 257, 610-612
43. Daniels, S. B. and Katzenellenbogen, J. A. (1986) Biochemistry 25, 1436-1444

44. Baek, D-J., Reed, P. E., Daniels, S. A., and Katzenellenbogen, J. A. (1990) Biochemistry 29, 4305-4311

45. Lin, L.-L., Lin, A. Y, and Knopf, J. L. (1992) Proc. Natl. Acad. Sci. USA 89, 6147-6151

46. Qiu, Z.-H. and Leslie, C. C. (1994) J. Biol. Chem. 269, 19480-19487

47. Qiu, Z.-H., Gij6n, M. A., de Carvalho, M. S., Spencer, D. M., and Leslie, C. C. (1998) J. Biol. Chem. 273, 8203-8211

48. Olivero, J. and Ganey, P. E. (1999) Toxicol. Appl. Pharm. 163, 9-16

49. Waggoner, D. W., Xu, J., Singh, I., Jasinska, R., Zhang, Q. X., Brindley, D. N. (1999) Biochim Biophys Acta 1439, 299-316

50. Nanjundan, M. and Possmayer, F. (2001) Biochem. J. 358, 637-646

51. Hooks, S. B., Santos, W. L., Im, D.-S., Heise, C. E., Macdonald, T. L., and Lynch, K. R. (2001) J. Biol. Chem. 276, 4611-4621

52. Ramanadham, S., Hsu, F-F., Bohrer, A., Ma, Z., and Turk, J. (1999) J. Biol. Chem. 274, 13915-13927

53. Channon, J. Y. and Leslie, C. C. (1990) J. Biol. Chem. 265, 5409-13

54. Glover, S., de Carvalho, M. S., Bayburt, T., Jonas, M., Chi, E., Leslie, C. C., and Gelb, M. H. (1995) J. Biol. Chem. 270, 15359-15367

55. Hirabayashi, T., Kume, K., Hirose, K, Yokomizo, T., Iino, A, Itoh, H., and Shimizu, T. (1999) J. Biol. Chem. 274, 5163-5169

56. Takuma, T. and Ichida, T. (1197) J. Biochem. 121, 1018-1024.

57. Wainter Irving W., Proposal For The Classification of High Performance Liquid Chromatograph Chiral Phases; How To Choose The Right Column. Trends In Analytical Chemistry Vol 6, no. 5, 1987

58. David W. Armstrong, Bonded Phase Material For Chromatographic Separations 1985 U.S. Pat. No. 4,539,399

59. Davankov V. A. Introduction to Chromatographic Resolution Of Enantiomers Chiral Separations by HPLC Ed A. M. Krstalovic Ellis Horwood ISBN 0-74580331-8

60. Davankov V. A. Resolution of Racemates By Ligand Exchange Chromatography Advances In Chromatography Vol 18 Marcel Dekker NY 1980 139

While the invention has been described with respect to various specific examples and embodiments thereof, it is understood that the invention is not limited thereto and many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A method of identifying whether a lipase enzyme is metabolically active within a cellular environment, said method comprising contacting said cellular environment with at least one of S-isomer bromoenal lactone (S-BEL) and R-isomer bromoenal lactone (R-BEL) and determining the identity of the lipase enzyme based on the interaction of the lipase enzyme with at least one of S-BEL and R-BEL, wherein the S-BEL selectively inhibits β phospholipase and the R-BEL selectively γ phospholipase.

2. A method in accordance with claim 1 wherein the lipase is contacted with S-BEL.

3. A method in accordance with claim 1 wherein the lipase is contacted with R-BEL.

4. A diagnostic kit for determining the metabolic activity of a lipase within a cellular environment, wherein said kit comprises a lipase for which it is desired to determine the metabolic activity, contacting said cellular environment with at least one of S-isomer bromoenal lactone (S-BEL) and R-isomer bromoenal lactone (R-BEL) and determining at least one of an identify and an activity of the lipase based on the interaction of said lipase with at least one of S-BEL and R-BEL, wherein the S-BEL selectively inhibits β phospholipase and the R-BEL selectively inhibits γ phospholipase.

5. A method of differentially inhibiting at least one of iPLA$_2$β and iPLA$_2$γ by contacting the same with S-isomer bromoenal lactone (S-BEL), observing a selectivity of S-BEL toward one of iPLA$_2$β or iPLA$_2$γ and determining that one of iPLA$_2$β or iPLA$_2$γ has been inhibited.

6. A method for pharmacologically distinguishing iPLA$_2$β from iPLA$_2$γ, said method comprising contacting a candidate iPLA$_2$ with S-BEL and if the S-isomer bromoenal lactone (S-BEL) is selective to the candidate iPLA$_2$, then determining that the iPLA$_2$ is iPLA$_2$β.

* * * * *